(12) United States Patent
Friend et al.

(10) Patent No.: US 10,265,647 B2
(45) Date of Patent: Apr. 23, 2019

(54) CENTRIFUGAL MICROFLUIDIC DEVICE

(75) Inventors: James Friend, Victoria (AU); Leslie Yu-Ming Yeo, Victoria (AU); Peggy Chan, Melbourne (AU); Nicholas Glass, Woolloongabba (AU); Richard Shilton, Pisa (IT)

(73) Assignee: Royal Melbourne Institute of Technology, Melbourne, Victoria (AU)

( * ) Notice: Subject to any disclaimer, the term of this patent is extended or adjusted under 35 U.S.C. 154(b) by 972 days.

(21) Appl. No.: 14/363,163

(22) PCT Filed: Jun. 22, 2012
(Under 37 CFR 1.47)

(86) PCT No.: PCT/AU2012/000732
§ 371 (c)(1),
(2), (4) Date: Apr. 2, 2015

(87) PCT Pub. No.: WO2013/082644
PCT Pub. Date: Jun. 13, 2013

(65) Prior Publication Data
US 2015/0231530 A1    Aug. 20, 2015

(30) Foreign Application Priority Data

Dec. 7, 2011   (AU) ............................... 2011905087

(51) Int. Cl.
*B01F 7/00*   (2006.01)
*B01L 3/00*   (2006.01)
(Continued)

(52) U.S. Cl.
CPC .......... *B01D 21/28* (2013.01); *B01F 7/00308* (2013.01); *B01F 11/0266* (2013.01);
(Continued)

(58) Field of Classification Search
CPC . B01D 21/28; B81C 1/00714; B01F 13/0001; B01F 11/0266; B01F 15/00493;
(Continued)

(56) References Cited

U.S. PATENT DOCUMENTS

2002/0097632 A1   7/2002  Kellogg et al.
2004/0115097 A1*  6/2004  Wixforth ............ B01F 11/0266
                                                          422/400
(Continued)

FOREIGN PATENT DOCUMENTS

WO   WO 97/21090   6/1997

OTHER PUBLICATIONS

Tjeung et al., Surface acoustic wave micromotor with arbitrary axis rotational capability, Nov. 21, 2011, Applied Physics Letters 99, 4 pages.*

(Continued)

*Primary Examiner* — David C Mellon
(74) *Attorney, Agent, or Firm* — BakerHostetler

(57) ABSTRACT

Disclosed is a centrifugal microfluidic device comprising a piezoelectric substrate; a rotatable platform device on the substrate; and at least one transducer on the substrate, the transducer being configured to generate a surface acoustic wave that propagates on the surface of the substrate and contacts the rotatable platform device asymmetrically to transfer energy thereto with a lateral distribution to cause rotation of the rotatable platform device. The device may be a microfluidic valve, a microfluidic mixer or a microfluidic particle concentrator.

17 Claims, 9 Drawing Sheets

(51) Int. Cl.
- B81B 7/02 (2006.01)
- B81C 1/00 (2006.01)
- B01D 21/28 (2006.01)
- B01F 11/02 (2006.01)
- B01F 13/00 (2006.01)
- B01F 15/00 (2006.01)
- B01J 19/00 (2006.01)
- F16K 99/00 (2006.01)
- G01N 21/07 (2006.01)

(52) U.S. Cl.
CPC ...... *B01F 13/0001* (2013.01); *B01F 13/0059* (2013.01); *B01F 15/00493* (2013.01); *B01J 19/0093* (2013.01); *B01L 3/50273* (2013.01); *B81B 7/02* (2013.01); *B81C 1/00714* (2013.01); *F16K 99/0063* (2013.01); *G01N 21/07* (2013.01); *B01J 2219/00889* (2013.01); *B01J 2219/00932* (2013.01); *B01L 2300/0803* (2013.01); *B01L 2300/161* (2013.01); *B01L 2400/0409* (2013.01); *B01L 2400/0436* (2013.01); *F16K 2099/0084* (2013.01); *Y10T 137/0391* (2015.04); *Y10T 137/206* (2015.04)

(58) Field of Classification Search
CPC .... B01F 13/0059; B01F 7/00308; B81B 7/02; F16K 99/0063; F16K 2099/0084; G01N 21/07; Y10T 137/206; Y10T 137/0391; B01J 19/0093; B01J 2219/00889; B01J 2219/00932; B01L 3/50273; B01L 2400/0409; B01L 2300/161; B01L 2300/0803; B01L 2400/0436
See application file for complete search history.

(56) References Cited

U.S. PATENT DOCUMENTS

| | | | | |
|---|---|---|---|---|
| 2004/0135470 | A1* | 7/2004 | Iseki | G02B 26/0858 310/313 R |
| 2008/0252171 | A1* | 10/2008 | Kirigaya | H02N 2/08 310/313 D |
| 2008/0269077 | A1 | 10/2008 | Lee et al. | |
| 2011/0111987 | A1 | 5/2011 | Siegrist et al. | |

OTHER PUBLICATIONS

Zhang et al. Surface acoustic wave motors and actuators: mechanism, structure, characteristic and application, Acoustic wavers, Oct. 2010, InTech, pp. 207-232. (Year: 2010).*
Bennes et al., Easy and versatile functionalization of lithium niobate wafers by hydrophobic trichlorosilanes, 2008, Applied Surface Science, 255, pp. 1796-1800. (Year: 2008).*
Cheng et al., Miniaturization of surface acoustic waves rotary motor, 2002, Ultrasonics, 39, pp. 591-594. (Year: 2002).*
Saiki et al., Micro liquid rotor operated by surface-acoustic wave, 2010, Microsystems Technology, 16, pp. 1589-1594. (Year: 2010).*
Cho et al., "One-Step Pathogen Specific DNA Extraction from Whole Blood on a Centrifugal Microfluidic Device", Lab Chip, 2007, 7, 4 pages.
Haeberle et al., "Centrifugal Extraction of Plasma from Whole Blood on a Rotating Disk", Lab Chip, 2006, 6, 776-781.
Haeberle et al., "Microfluidic Platforms for Lab-on-a-Chip Applications", Lab Chip, 2007, 7(9), 1094-1110.
Lafleur et al., "Pre-Concentration of Trace Metals on Centrifugal Microfluidic Discs with Direct Determination by Laser Ablation Inductively Coupled Plasma Mass Spectrometry", J Analytical Atomic Spectrometry, 2009, 24,•1511-1516.
Li et al., "Out-of-Plane Microvalves for Whole Blood Separation on Lab-on-a-CD", Micromech Microeng, 2010, 20, 105024, 10 pages.
Riegger et al., "Single-Step Centrifugal Hematocrit Determination on a 10-$ Processing Device", Biomed Microdev, 2007,9, 795-799.
Shih et al., "Supernatant Decanting on a Centrifugal Platform", Biomicrofluidics; 2011, 5(1), 013414, 9 pages.
Shilton et al., "On-Chip Surface Acoustic Wave Driven Microfluidic Motors", Proc. of SPIE, 2011, 8204, 6 pages.
Shilton et al., "Particle Concentration and Mixing in Microdrops Driven by Focused Surface Acoustic Waves", J. Appl. Phys., 2008 104, 014910, 9 pages.
Shilton et al., "Rotational Microfluidic Motor for On-Chip Microcentrifugation", Applied Physics Letters, 2011, 98, 254103, 3 pages.
"Smart Nano+ Micro Materials and Devices—Technical Program, Connecting Minds for Global Solutions", Symposium, Swinburne Univ. of Technology/Hawthorn Campus, Melbourne, Australia, Dec. 4-7, 2011, 20 pages.

* cited by examiner

CENTRIFUGAL MICROFLUIDIC DEVICE

CROSS-REFERENCE TO RELATED APPLICATIONS

This application is the National Stage of International Application No. PCT/AU2012/000732, filed Jun. 22, 2012, which claims the benefit of Australian Application No. 2011905087, filed Dec. 7, 2011, the disclosures of which are incorporated herein by reference in their entireties.

TECHNICAL FIELD

The present invention relates generally to devices for maneuvering fluids on microfluidic platforms and, more specifically, to microfluidic devices that utilise centrifugal force to manoeuvre fluids in microfluidic structures.

BACKGROUND

Microfluidic devices, such as laboratories-on-a-chip, are becoming increasingly important in applications in the fields of genomics, drug screening, and other clinical applications. In conventional microfluidic devices, small volumes of liquid are maneuvered within a network of microfluidic channels to achieve a variety of chemical, physical, and/or biological processes. Microfluidic devices such as these use a system of pumps, channels, valves, and mixing elements to manipulate the fluids.

Pressure is generally required to manoeuvre a fluid within a microfluidic device. In some devices, capillary pressure or pressure generated by a pump is used to push a fluid through a network of microfluidic channels. Electrokinetic pumping is often used for this purpose but it unfortunately has some disadvantages. Firstly, electrokinetic pumping is sensitive to the physicochemical properties, such as ionic strength and pH, of the fluid. As a result, it is difficult to pump biological fluids, such as blood and urine, by this method. Secondly, electrokinetic pumping requires continuity in the fluid in the channels and, therefore, it does not work in the presence of trapped bubbles (e.g., air), and care has to be taken to ensure that the channels are free of bubbles.

An alternative pumping method is based on centrifugal force. The lab-on-a-CD platform (Haeberle et al., *Lab Chip*, 2007, 7, 1094-1110) relies on centrifugal pumping and has received considerable attention to date. The use of centrifugal pumps to manoeuvre fluids within microfluidic systems has been described, for example, in published United States patent application Nos. 20020097632 (Kellog et al.), 20080269077 (Lee et al.), and 20110111987 (Siegrist et al.). However, the known centrifugal pumps use rotational motors that make the pumps difficult to miniaturise to a point where they are suitable for lab-on-a-chip type applications.

There is a need for microfluidic devices that overcome one or more of the problems associated with prior art devices and/or microfluidic devices that provide alternatives to prior art devices.

SUMMARY

The present invention arises from our research into the use of surface acoustic waves (SAWs) to apply forces to fluid droplets and rotors on a surface. We have previously found that when SAWs are directed at an edge of a fluid droplet the energy transferred to the droplet affects bulk liquid recirculation within the droplet and we have now further developed and utilised this effect to rotate platforms or discs on microfluidic devices.

In a first aspect, the present invention provides a centrifugal microfluidic device comprising:
  a piezoelectric substrate;
  a rotatable platform device on the substrate; and
  at least one transducer on the substrate, the transducer being configured to generate a surface acoustic wave that propagates on the surface of the substrate and contacts the rotatable platform device asymmetrically to transfer energy thereto with a lateral distribution to cause rotation of the rotatable platform device.

In embodiments, the rotatable platform device comprises a platform comprising a microfluidic structure on an upper surface thereof. In embodiments, the microfluidic structure comprises at least one microfluidic channel. For example, the microfluidic structure may comprise at least one fluid reservoir in fluid communication with the at least one microfluidic channel forming a fluid flow path from the reservoir, the microfluidic structure transmitting fluid from the fluid reservoir using centrifugal force due to rotation of the rotatable platform device. In embodiments, the microfluidic structure further comprises a functional unit in fluid communication with the at least one microfluidic channel, the functional unit capable of receiving the fluid from the microfluidic channel and performing at least one function when in contact with the fluid. The microfluidic structure may also include one or more inlet ports and one or more outlet ports.

In a second aspect, the present invention provides a microfluidic valve comprising:
  a piezoelectric substrate;
  a rotatable platform device on the substrate, the rotatable platform device comprising a platform comprising a microfluidic structure comprising an inlet reservoir in fluid connection via a radially disposed microfluidic channel with an outlet reservoir, the inlet reservoir positioned radially inwardly of the outlet reservoir; and
  at least one transducer on the substrate, the transducer being configured to generate a surface acoustic wave that propagates on the surface of the substrate and contacts the rotatable platform device asymmetrically to transfer energy thereto with a lateral distribution to cause rotation of the platform such that when the radial acceleration resulting from rotation of the platform is greater than the capillary force retarding the meniscus of a fluid in the inlet reservoir the fluid passes from the inlet reservoir to the outlet reservoir.

In a third aspect, the present invention provides a microfluidic mixer comprising:
  a piezoelectric substrate;
  a rotatable platform device on the substrate, the rotatable platform device comprising a platform comprising a microfluidic structure comprising at least two inlet reservoirs each of which is in fluid connection via a radially disposed microfluidic channel with a common outlet reservoir, the inlet reservoirs positioned radially inwardly of the outlet reservoir; and
  at least one transducer on the substrate, the transducer being configured to generate a surface acoustic wave that propagates on the surface of the substrate and contacts the rotatable platform device asymmetrically to transfer energy thereto with a lateral distribution to cause rotation of the platform such that when the radial acceleration resulting from rotation of the platform is greater than the capillary force retarding the meniscus of a fluid in each of the inlet reservoirs each fluid passes from each inlet reservoir to the outlet reservoir.

In a fourth aspect, the present invention provides a microfluidic particle concentrator comprising:
a piezoelectric substrate;
a rotatable platform device on the substrate, the rotatable platform device comprising a platform comprising a microfluidic structure comprising at least one radially extending reservoir; and
at least one transducer on the substrate, the transducer being configured to generate a surface acoustic wave that propagates on the surface of the substrate and contacts the rotatable platform device asymmetrically to transfer energy thereto with a lateral distribution to cause rotation of the platform such that particles in a particle laden fluid contained in the radially extending reservoir are concentrated in a region of the reservoir following the rotation.

The rotatable platform device may comprise a platform configured as a rotor and positioned directly on the substrate or, alternatively, it may comprise a platform positioned on a fluid coupling layer which is, in turn, positioned on the substrate.

In those embodiments in which the rotatable platform device comprises a platform configured as a rotor, the rotor may comprise a disc having indents on the circumference or it may comprise a plurality of radially extending rotor arms. In some embodiments, the rotor is journalled for rotation on a central pin which extends from the substrate. In these embodiments, the at least one transducer on the piezoelectric substrate is configured to generate a surface acoustic wave that propagates on the surface of the substrate and contacts the rotor asymmetrically to transfer energy thereto with a lateral distribution to cause rotation of the rotor (i.e. the platform).

In those embodiments in which the rotatable platform device comprises a platform and a fluid coupling layer, the fluid coupling layer is on a region of the substrate and between the substrate and the platform. In these embodiments, the at least one transducer on the piezoelectric substrate is configured to generate a surface acoustic wave that propagates on the surface of the substrate and contacts the fluid coupling layer asymmetrically to transfer energy thereto with a lateral distribution to cause rotation of the fluid coupling layer and platform.

In embodiments of the first to fourth aspects of the invention, the piezoelectric substrate comprises a hydrophobic surface.

In embodiments of the first to fourth aspects of the invention, the substrate further comprises a non-hydrophobic region within the hydrophobic surface.

In embodiments of the first to fourth aspects of the invention having a fluid coupling layer, the fluid coupling layer comprises a droplet of hydrophilic liquid positioned within the non-hydrophobic region.

In embodiments of the first to fourth aspects of the invention, the transducers are interdigital transducers. The interdigital transducers may be aluminium single-phase unidirectional electrodes.

In embodiments of the first to fourth aspects of the invention, the transducers are focusing transducers. The transducers may have an elliptical focus.

In embodiments of the first to fourth aspects of the invention, the piezoelectric substrate Comprises 127.68° lithium niobate wafers.

In a fifth aspect, the present invention provides a microfluidic system comprising:

a microfluidic device of the first aspect of the invention and/or a microfluidic valve of the second aspect of the invention and/or a microfluidic mixer of the third aspect of the invention and/or a microfluidic particle concentrator of the fourth aspect of the invention; and
a transducer control unit for controllably powering the transducer(s).

In embodiments, the transducer control unit comprises an RF signal generator for exciting the transducer(s) and generating the surface acoustic wave.

In a sixth aspect, the present invention provides a method of fabricating a centrifugal microfluidic device, the method comprising:
providing a piezoelectric substrate;
forming at least one transducer on the surface of the substrate;
masking the at least one transducer and a non-hydrophobic region of the surface of the substrate;
depositing a hydrophobic surface on the surface of the masked substrate;
removing the masks from the substrate;
depositing a drop of a hydrophilic liquid on the non-hydrophobic region; and
placing a rotatable platform comprising a microfluidic structure on the drop so as to form a fluid coupling layer between the substrate and the rotatable platform.

In a seventh aspect, the present invention also provides a method for rotating a platform comprising:
coupling the platform to a piezoelectric substrate;
propagating a surface acoustic wave along the substrate, the surface acoustic wave configured to cause rotation of the platform.

In embodiments of the seventh aspect of the invention, the surface acoustic wave is configured to contact the platform asymmetrically to transfer energy thereto with a lateral distribution to cause rotation of the platform.

DESCRIPTION OF EMBODIMENTS

It is to be understood that the following description is for the purpose of describing particular embodiments only and is not intended to be limiting with respect to the above description.

The present invention provides, in a first aspect, a centrifugal microfluidic device. The device comprises a piezoelectric substrate with a rotatable platform device on the substrate. At least one transducer is positioned on the piezoelectric substrate. The transducer is configured to generate a surface acoustic wave that propagates on the surface of the substrate and contacts the rotatable platform device asymmetrically to transfer energy thereto with a lateral distribution to cause rotation of the rotatable platform device.

The microfluidic device may be any device that requires pumping of a fluid through a microfluidic channel or network. Microfluidic devices of this type typically have an analytical, synthetic or preparative purpose in the areas of life sciences, organic chemistry, analytical chemistry, inorganic chemistry, physical chemistry, etc. Operations that may be carried out on the microfluidic devices include separations, affinity reactions, chemical reactions, biochemical reactions, detection, etc. For example, the microfluidic device may be used for blood plasma separation (Haeberle et al., *Lab Chip*, 2006, 6, 776-781; Li et al., *Micromech Microeng*, 2010, 20, 105024; Shih et al., *Biomicrofluidics*, 2011, 5, 013414; each incorporated herein by reference), on-chip blood diagnostics (Riegger et al., *Biomed Microdev*, 2007, 9, 795-799; incorporated herein by reference), extractions (Cho et al., *Lab Chip,* 2007, 7, 565-573; incorporated herein by reference), and concentration steps (Lafleur et al., *J Anal At Spectrom,* 2009, 24, 1511-1516; incorporated herein by reference).

As used herein, the term "microfluidic" means that one or more fluid volumes in the microliter (µl) or below range is transported and processed within a microchannel structure of the device. Microfluidic devices typically transport nanoliter and picoliter fluid volumes.

As used herein, the term "surface acoustic wave" is intended to mean a nanometer order amplitude electrostatic wave that propagates along the surface of a substrate.

In embodiments of the invention, the rotatable platform device comprises a platform and a fluid coupling layer. The fluid coupling layer is on a region of the substrate and between the substrate and the platform. In these embodiments, the invention is predicated, at least in part, on the finding that surface acoustic waves are able to drive microcentrifugation in a sessile fluid drop through symmetry breaking of the planar wave such that the acoustic radiation is imparted into the drop with a lateral distribution to thereby cause rotation within the drop. Thus, the at least one transducer on the piezoelectric substrate is configured to generate a surface acoustic wave that propagates on the surface of the substrate and contacts the fluid coupling layer asymmetrically to transfer energy thereto with a lateral distribution to cause rotation of the fluid coupling layer and platform.

Thus, in embodiments, the present invention provides a centrifugal microfluidic device comprising a piezoelectric substrate with a rotatable platform device on the substrate, the rotatable platform device comprising a fluid coupling layer on a region of the substrate and a rotatable platform positioned on the fluid coupling layer. At least one transducer is positioned on the piezoelectric substrate. The transducer is configured to generate a surface acoustic wave that propagates on the surface of the substrate and contacts the fluid coupling layer asymmetrically to transfer energy thereto with a lateral distribution to cause rotation of the rotatable platform device.

As already mentioned, in the device of the present invention the coupling of the surface acoustic waves into the fluid coupling layer results in rotation of the fluid coupling layer and, hence, the rotatable platform. The rotation within the fluid coupling layer, an azimuthal form of acoustic streaming, is rapid, typically on the order of several cm/s. This has resulted in the development of an on-chip centrifugal micromotor, where the azimuthal streaming in the fluid coupling layer is capable of rotating the rotatable platform up to almost 10,000 rpm. Typically, rotation speeds of up to about 1500 rpm can be generated for 10 mm diameter, 300 µm thick rotatable platforms on which microchannels are patterned. The associated radial acceleration of approximately $10^2$ m/s$^2$ at the outer regions of the rotatable platform can be exploited to drive a number of microfluidic processes, as described herein. Advantageously, it is now possible to fabricate a disposable device that is significantly smaller than existing devices and without the need for additional moving parts or rotational motors therefore eliminating potential wear problems and offering the simplicity and down scalability of solid-state actuation.

In other embodiments of the invention, the rotatable platform device comprises only a rotor positioned directly on the substrate. The rotor may comprise a disc having indents on the circumference or it may comprise a plurality of radially extending rotor arms.

In these embodiments, the invention is predicated, at least in part, on the finding that surface acoustic waves can cause rotation of 1 mm diameter rotors with a simple, miniaturisable design. We have found that the rotor-substrate interaction is stiction-mediated in a way that may be useful for characterising high-speed frictional micro/nanoscale phenomena and that rotation can be driven at radial velocities over an order of magnitude faster that those previously described, with no moving parts other than the rotor itself.

In embodiments, the device comprises one transducer on the piezoelectric substrate, the transducer being configured to generate a surface acoustic wave that propagates on the surface of the substrate and contacts the rotatable platform device asymmetrically to transfer energy thereto with a lateral distribution to cause rotation of the rotatable platform device.

As used herein, the term "asymmetric" when used in relation to a surface acoustic wave contacting a rotatable platform device means that there is an asymmetric distribution of acoustic radiation along the width of the rotatable platform device transverse to the radiation propagation direction.

In embodiments, the lateral distribution of the acoustic energy into the rotatable platform device is achieved by contacting an edge region of the rotatable platform device that is offset laterally with respect to the centre of the rotatable platform device. In these embodiments, the transducer may be offset laterally with respect to the centre of the rotatable platform device and the surface acoustic wave that is generated therefrom propagates on the surface of the substrate and contacts an edge region of the rotatable platform device that is offset laterally with respect to the centre of the rotatable platform device.

In other embodiments, the transducer may be positioned on the substrate symmetrically with respect to the centre of the rotatable platform device and a SAW dissipating device is positioned between the transducer and the rotatable platform device, wherein the SAW dissipating device blocks part of the surface acoustic wave that would otherwise be incident centrally on the rotatable platform device.

In still other embodiments, the transducer is offset laterally with respect to the centre of the rotatable platform device or in line with the centre of the rotatable platform device and the surface acoustic wave is focussed at the edge region of the rotatable platform device that is offset laterally with respect to the centre of the rotatable platform device.

In still other embodiments, the transducer is a tapered interdigital transducer (T-IDT) or a stepped interdigital transducer (S-IDT) that tapers from adjacent one side of the piezoelectric substrate to adjacent the opposing side of the substrate such that opposing edge regions of the rotatable platform device are subjected to surface acoustic waves of different frequency.

Whilst it is possible to use a single transducer to cause rotation of the rotatable platform device, it is also possible to use any number of transducers in a single device. Therefore, in embodiments the device comprises two or more transducers, each transducer being configured to generate a surface acoustic wave that propagates on the surface of the substrate and contacts the rotatable platform device to transfer energy thereto with a lateral distribution. In these embodiments, opposing surface acoustic waves are generated by opposing transducers that are positioned on the piezoelectric substrate. The opposing transducers may each be laterally offset about the centre of the rotatable platform device. The opposing transducers may be positioned on the piezoelectric substrate and laterally offset symmetrically about the centre of the rotatable platform device. Alternatively, each of the opposing transducers may be positioned on the substrate in line with the centre of rotatable platform device and a SAW dissipating device may be positioned between each transducer and the rotatable platform device, wherein the SAW dissipating device blocks part of the surface acoustic wave that would otherwise be incident centrally on the rotatable platform device.

Transducers for generating surface acoustic waves are known in the art. Interdigital transducers (IDTs) are particularly suitable for generating surface acoustic waves. Interdigital transducers comprise a finger-like periodic pattern of parallel in-plane electrodes. Adjacent fingers from opposing electrodes form finger pairs. When a radio frequency signal is applied to the finger pairs a spatially periodic, surface-concentrated electric field distribution is established between the electrode fingers and it penetrates into the piezoelectric substrate. As a result of the piezoelectric coupling, an elastic strain distribution with periodicity is created in the substrate, thereby generating a surface acoustic wave.

In embodiments, each of the transducers comprises one pair of electrode fingers. However, it is also contemplated that each transducer may comprise a number of pairs of fingers. For example, in some other embodiments of the device of the present invention, each of the transducers comprises thirty finger pairs.

The interdigital transducer may be a straight IDT, a focused IDT or a tapered IDT.

The interdigital transducers may comprise single-phase unidirectional electrodes (SPUDTs). The SPUDT may be a focused SPUDT, a straight SPUDT or a tapered SPUDT.

The interdigital transducers may be formed on the surface of the piezoelectric substrate by photolithography and surface etching (Shilton et al. *J App Phys*, 2009, 104, 014910).

The finger width and spacing of the fingers in each interdigital transducer may be configured for a specific, predetermined surface acoustic wave frequency. The surface acoustic wave frequency may be from about 20 MHz to 1 GHz or higher. In some embodiments, the surface acoustic wave frequency is about 30 MHz. For example, in some embodiments the surface acoustic wave frequency is about 29.7 MHz. To generate the surface acoustic wave, an oscillating electrical signal matching the operating frequency is applied to the transducers using a radio frequency (RF) signal generator and, if necessary, a power amplifier. The surface acoustic wave then propagates across the surface of the piezoelectric substrate as a Rayleigh wave. The surface acoustic wave generated has a wavelength $\lambda$ which is set by the finger width and spacing.

The strength of the surface acoustic wave that is generated can be controlled by changing the overlap of the electrodes, number of finger pairs, their periodicity, the finger pattern, and the power input.

In embodiments, the transducers are focusing transducers. The configuration of the electrodes in a transducer can be used to vary the shape of the focus of the surface acoustic waves generated. For example, the transducer may be configured to have a generally curved, circular or elliptical focus. In some embodiments of the devices described herein, the transducers have an elliptical focus.

In other embodiments, the transducers are tapered interdigital transducers (T-IDTs). T-IDTs may be used to produce surface acoustic waves of different frequencies and when the different frequencies are incident on the rotatable platform device there is a lateral distribution of the energy imparted on the rotatable platform device.

As discussed, in embodiments the or each transducer is laterally offset relative to the centre of the rotatable platform device. As used herein, the term "laterally offset" means positioned to a side of a line that passes through the centre of the rotatable platform device. If more than one transducer is used the transducers oppose one another in the sense that they are positioned diametrically opposite one another about the rotatable platform device. The transducers are positioned at an equal radial distance from the rotatable platform device. As such, the transducers are positioned symmetrically about the rotatable platform device. In this configuration, the transducers generate mutually opposing acoustic radiation that couples at opposing edges of the rotatable platform device which, in the embodiments in which the rotatable platform device comprises a fluid coupling layer, drives acoustic streaming in the fluid of the fluid coupling layer and consequent azimuthal fluid motion.

In other embodiments, the or each transducer is a straight IDT or SPUDT that is positioned on the substrate in line with the centre of the rotatable platform device. A SAW dissipating device is positioned between the or each transducer and the rotatable platform device. The SAW dissipating device blocks part of the surface acoustic wave that would otherwise be incident centrally on the rotatable platform device. The SAW dissipating device may be an acoustic barrier formed from any acoustically lossy material. A range of materials that provide acoustic attenuation could be used as an energy dissipating material, such as polydiemthylsiloxane (PDMS), silicone and many polymers. For example, the SAW dissipating device may be in the form of an energy dissipating polymer strip on the surface of the substrate. By way of example, the energy dissipating polymer may be First Contact™ Polymer (Photonic Cleaning Technologies, Platteville, Wis., USA). Other energy dissipating polymers that could be used include those containing rubber with a low cross link density. Block copolymers in which the majority component is an amorphous rubber may also be suitable. In these materials, dissipation of mechanical energy occurs primarily through viscous mechanisms that depend, on a molecular scale, on the frictional coefficient between a polymer chain and its surroundings. In alternative embodiments, the energy could be reflected using reflecting electrodes to reflect the travelling acoustic wave.

In other embodiments, the or each transducer is a tapered interdigital transducer (T-IDT) or a stepped interdigital transducer (S-IDT) each of which tapers from adjacent one side of the piezoelectric substrate to adjacent the opposing side of the substrate such that each transducer produces surface acoustic waves of different frequency such that there is a lateral distribution of the energy imparted on the rotatable platform device. In these embodiments, the substrate may comprises two opposing T-IDTs or S-IDTs wherein the IDTs are flipped with respect to one another, meaning that the surface acoustic waves propagate in an antisymmetric fashion. These IDTs generate waves at specific positions depending on what frequency is applied to actuate it. Using T-IDTs or S-IDTs in this way it is possible to: change the direction of rotation of the disc by changing the frequency; change the speed of rotation of the disc by changing the frequency (in addition to changing the speed of ration by changing the input voltage/power); and/or focus the surface acoustic waves in the device by changing the frequency (possibly for mixing and/or particle concentration).

In embodiments, the piezoelectric substrate is planar and may be formed from any suitable piezoelectric material. The piezoelectric substrate may be formed from a suitable piezoelectric material, such as ST-quartz, zinc oxide (ZnO), aluminum nitride (AlN), lithium niobate (LiNbO$_3$), or lithium tantalate (LiTaO$_3$). In embodiments, the piezoelectric substrate comprises a strong piezoelectric material, such as 127.68° lithium niobate, which has a large electromechanical coupling coefficient. The piezoelectric substrate may also be a piezoelectric optical material, such as lithium niobate, which enables the combination of fluid handling and optical detection using total internal reflection fluorescence.

The piezoelectric substrate may be a multilayer arrangement comprising a piezoelectric layer on a rigid, non-piezoelectric substrate. The non-piezoelectric substrate may be glass or a semiconductor substrate. The piezoelectric layer may be deposited on the rigid, non-piezoelectric substrate to a depth that is thicker than the surface acoustic wave penetration depth by sputtering or sol-gel methods.

The microfluidic device may also comprise an acoustic waveguide to confine the lateral extent of at least one of the surface acoustic waves on the surface of the substrate. Alternatively, or in addition, the device may comprise an energy dissipating edge material at the edges of the piezoelectric substrate. The energy dissipating material minimises wave reflections at the edges of the device.

In embodiments, the piezoelectric substrate further comprises a hydrophobic surface. As used herein, the term "hydrophobic surface" is intended to mean a surface that has an equilibrium liquid contact angle of ≥90° (in particular for water and other aqueous media), whilst the terms "non-hydrophobic surface" and "hydrophilic surface" are intended to mean a surface that has an equilibrium liquid contact angle of ≤90°.

The hydrophobic surface can be formed by depositing a hydrophobic material, such as a plastic or polyfluorocarbon, on the piezoelectric substrate. An example of a suitable hydrophobic material is polytetrafluoroethylene (PTFE). PTFE is commercially available as Teflon®. The hydrophobic surface may be deposited on the surface of the piezoelectric substrate using any suitable coating technique, including spin coating, dip coating, spray coating, printing, vapor deposition, etc. In some embodiments, the hydrophobic surface is deposited on the surface of the piezoelectric substrate by spin coating.

In embodiments, the hydrophobic surface does not cover the entire surface of the piezoelectric substrate and, as a result, there are regions on the piezoelectric substrate that do not have a hydrophobic surface. In those embodiments in which the rotatable platform device comprises a fluid coupling layer, the substrate has a non-hydrophobic region that is formed within the hydrophobic surface. The surface in the non-hydrophobic region is different to the hydrophobic surface and is compatible with a hydrophilic liquid, such as water. A wide range of hydrophilic liquids could be used to form the fluid coupling layer in these embodiments. From a practical point of view, rotation is slowed at high viscosities and, therefore, any liquid having a viscosity of about 1000 cp or less could be used. In embodiments, the hydrophilic liquid is selected from the group consisting of: water, glycerol, and combinations thereof. Silicone oils or similar may also be used and an advantage of these materials is that it is possible to tailor the viscosity of the fluid.

The non-hydrophobic region in these embodiments is circular and accommodates a drop of the hydrophilic liquid which forms the fluid coupling layer when the rotatable platform is placed thereon. The hydrophilic liquid is incompatible with the hydrophobic surface and, therefore, is retained within the non-hydrophobic region. The diameter of the non-hydrophobic region will depend on the size of the piezoelectric substrate and/or the rotatable platform. In embodiments, the diameter of the non-hydrophobic region is from about 5 mm to about 20 mm. In embodiments, the diameter of the non-hydrophobic region is from about 8 mm to about 12 mm. In embodiments, the diameter of the non-hydrophobic region is about 10 mm.

In embodiments, the non-hydrophobic region is in the form of a well in the surface of the piezoelectric substrate.

The non-hydrophobic region is formed by masking the surface of the piezoelectric substrate, coating the substrate with the hydrophobic material as described previously, and then removing the mask. If required, the surface of the non-hydrophobic region may be further modified to improve one or more properties of the surface, such as the hydrophilicity.

It will be appreciated from the above description that the fluid coupling layer comprises a droplet of hydrophilic liquid positioned within the non-hydrophobic region. The rotatable platform is placed on to of the droplet of hydrophilic liquid. In embodiments, the rotatable platform is a circular disc having an upper surface and a lower surface. The lower surface is in contact with the hydrophilic liquid droplet and the upper surface comprises a microfluidic structure extending in a plane parallel to the plane of the platform.

The platform which is part of the rotatable platform device may be fabricated from a suitable photoresist material. Suitable materials for this purpose include any of the commercially available epoxy-based photoresist materials, such as SU-8. Other materials that could be used include, but are not limited to, PDMS and practically any other polymer, silicon, glass, metals, or any combination thereof. For example, PDMS could be bonded to glass to make the platform.

A microfluidic structure of desired configuration can be formed on the upper surface of the platform of the rotatable platform device using any micro- or nano-fabrication techniques including, but not limited to, photolithography, microcontact printing or nanoimprint lithography. To do this, a base layer may be masked and then a second layer of material deposited on the base layer. The second layer may be deposited using any suitable coating technique although vapour deposition is particularly suitable for this purpose. The thickness of the second layer that is deposited will determine the depth of the microfluidic channels, reservoirs, etc formed on the rotatable platform. The thickness of the second layer (and hence the depth of the channels) may be from about 100 µm to about 500 µm. In embodiments, the thickness of the second layer is from about about 100 µm to about 300 µm. In embodiments, the thickness of the second layer is about 200 µm.

The microfluidic structure may comprise at least one fluid reservoir in fluid communication with at least one microfluidic channel forming a fluid flow path from the reservoir, the microfluidic structure transmitting fluid from the fluid reservoir using centrifugal force due to rotation of the rotatable platform. The microfluidic structure may also comprise a functional unit in fluid communication with the at least one microfluidic channel, the functional unit capable of receiving the fluid from the microfluidic channel and performing at least one function when in contact with the fluid. The microfluidic structure may also include one or more inlet ports and one or more outlet ports. The microfluidic structure thus may comprise one, two, three or more units selected amongst inlet ports, outlet ports, reservoirs for distributing samples, liquids and/or reagents to individual microfluidic structures, microfluidic channels for liquid transport, units for defining liquid volumes, valving units, units venting to ambient atmosphere, units for mixing liquids, units for performing chemical reactions or bioreactions, units for separating soluble constituents or particulate materials from a liquid phase, waste liquid units including waste cavities and overflow channels, detection units, units for collecting an aliquot processed in the structure and to be transferred to another device e.g., for analysis, branching units for merging or dividing a liquid flow, etc. The microfluidic structure may contain several inlet ports and/or several outlet ports that are connected to a main flow path via microfluidic channels at a different or at the same downstream position. These microfluidic channels may also contain functional units of the type discussed above.

The microfluidic channels may be open or enclosed channels. The cross-section of the microfluidic channels may be circular, ellipsoid etc. Alternatively, the microfluidic channels may have inner edges, i.e., have cross-sections that are triangular, square, rectangular, partly rounded, planar etc.

The inner surfaces of the microfluidic structures may be functionalised. For example, all or part of the inner surface may be coated with a hydrophilic polymer.

The microfluidic device of the present invention may be used as a stand alone device or it may be used as one or more of the components of a more complex microfluidic system. There are various typical units in a microfluidic device, including valves, volume metering, mixing and flow switching. These types of units can make up structures that can be used in a variety of ways.

In embodiments, the microfluidic device of the present invention may function as a valve. Thus, the present invention also provides a microfluidic valve comprising:
  a piezoelectric substrate;
  a rotatable platform device on the substrate, the rotatable platform device comprising a platform comprising a microfluidic structure comprising an inlet reservoir in fluid connection via a radially disposed microfluidic channel with an outlet reservoir, the inlet reservoir positioned radially inwardly of the outlet reservoir; and
  at least one transducer on the substrate, the transducer being configured to generate a surface acoustic wave that propagates on the surface of the substrate and contacts the rotatable platform device asymmetrically to transfer energy thereto with a lateral distribution to cause rotation of the platform such that when the radial acceleration resulting from rotation of the platform is greater than the capillary force retarding the meniscus of a fluid in the inlet reservoir the fluid passes from the inlet reservoir to the outlet reservoir.

In embodiments, the microfluidic device of the present invention may function as a microfluidic mixer. Thus, the present invention also provides a microfluidic mixer comprising:
  a piezoelectric substrate;
  a rotatable platform device on the substrate, the rotatable platform device comprising a platform comprising a microfluidic structure comprising at least two inlet reservoirs each of which is in fluid connection via a radially disposed microfluidic channel with a common outlet reservoir, the inlet reservoirs positioned radially inwardly of the outlet reservoir; and
  at least one transducer on the substrate, the transducer being configured to generate a surface acoustic wave that propagates on the surface of the substrate and contacts the rotatable platform device asymmetrically to transfer energy thereto with a lateral distribution to cause rotation of the platform such that when the radial acceleration resulting from rotation of the platform is greater than the capillary force retarding the meniscus of a fluid in each of the inlet reservoirs each fluid passes from each inlet reservoir to the outlet reservoir.

In embodiments, the microfluidic device of the present invention may function as a microfluidic particle concentrator. Thus, the present invention also provides a microfluidic particle concentrator comprising:
  a piezoelectric substrate;
  a rotatable platform device on the substrate, the rotatable platform device comprising a platform comprising a microfluidic structure comprising at least one radially extending reservoir; and
  at least one transducer on the substrate, the transducer being configured to generate a surface acoustic wave that propagates on the surface of the substrate and contacts the rotatable platform device asymmetrically to transfer energy thereto with a lateral distribution to cause rotation of the platform such that particles in a particle laden fluid contained in the radially extending reservoir are concentrated in a region of the reservoir following the rotation.

Any one or all of the aforementioned aspects of the invention may be used in a microfluidic system. In addition to the microfluidic device, the microfluidic system may comprise a transducer control unit for controllably powering the transducers. In embodiments, the transducer control unit comprises an RF signal generator for exciting the opposing transducers and generating the opposing surface acoustic waves.

The present invention also provides a method of fabricating a centrifugal microfluidic device, the method comprising:
  providing a piezoelectric substrate;
  forming at least one transducer on the surface of the substrate;
  masking the transducer(s) and a non-hydrophobic region of the surface of the substrate;
  depositing a hydrophobic surface on the surface of the masked substrate;
  removing the masks from the substrate;
  depositing a drop of a hydrophilic liquid on the non-hydrophobic region; and
  placing a rotatable platform comprising a microfluidic structure on the drop so as to form a fluid coupling layer between the substrate and the rotatable platform.

Any of the steps of the fabrication method may be carried out as described herein with reference to the examples.

The present invention also provides a method for rotating a platform comprising:
  coupling the platform to a piezoelectric substrate;
  propagating a surface acoustic wave along the substrate, the surface acoustic wave configured to cause rotation of the platform.

In embodiments, the surface acoustic wave is configured to contact the platform asymmetrically to transfer energy thereto with a lateral distribution to cause rotation of the platform.

The invention is further described by way of the following non-limiting examples.

BRIEF DESCRIPTION OF THE FIGURES

Illustrative embodiments of the present invention will be discussed with reference to the accompanying drawings wherein.

In the following description, like reference characters designate like or corresponding parts throughout the figures.

EXAMPLES

Figure 7:
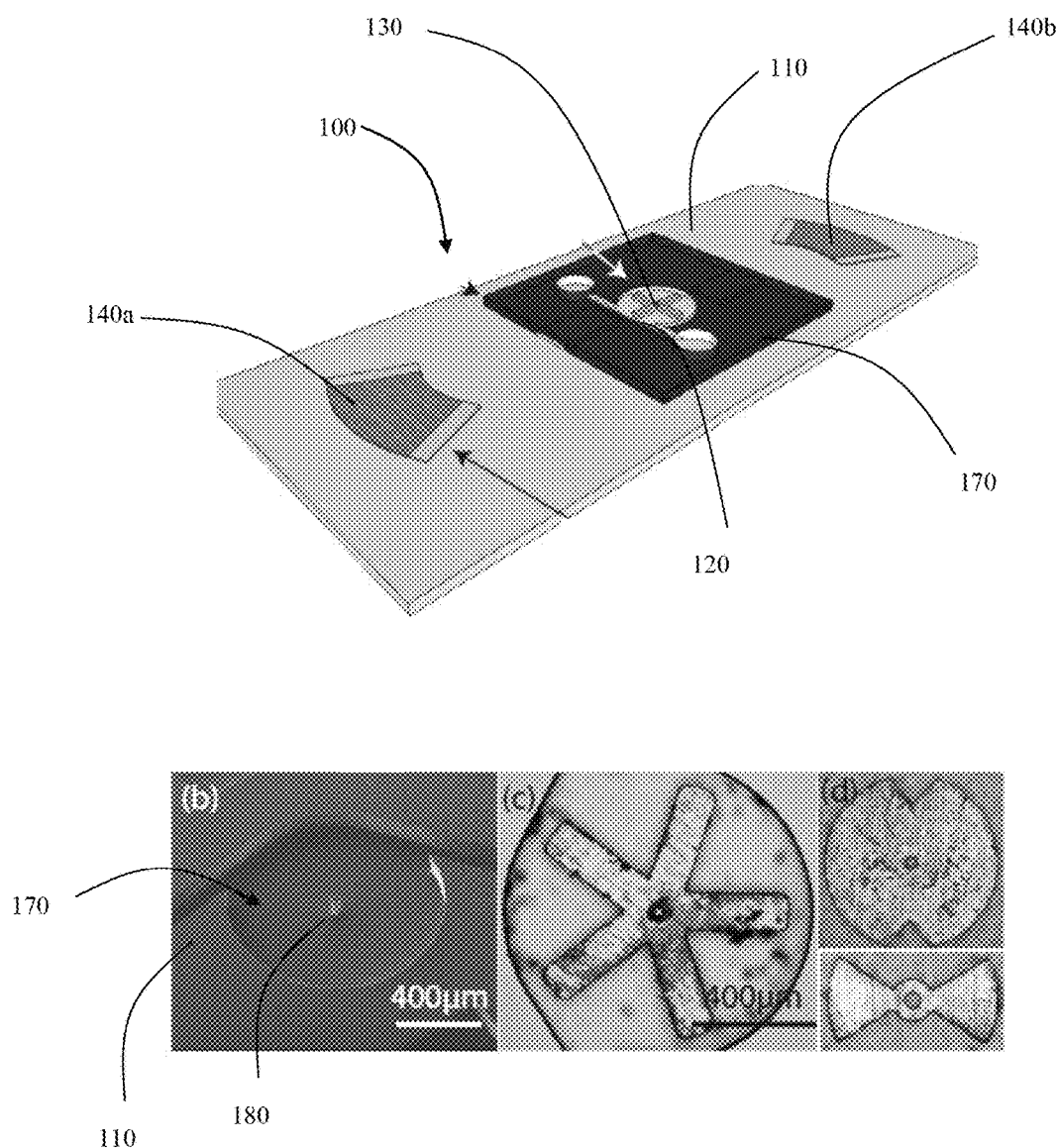
FIG. 7(a) shows a representation (not to scale) of an alternative embodiment of a microfluidic device with no fluid coupling layer; the entire device is around 32 mm×12 mm×1 mm and the top of the Si chamber is shown open for clarity; (b) is a scanning electron microscope (SEM) image of the Si chamber used to house the rotors; this is viewed from the side that is bonded to the piezoelectric substrate; note the 40 μm diameter Si central pin used to mount the rotors; (c) is a SEM image of the miniaturized (~55 μm) thick steel rotor in an 80 μm deep, 1 mm diameter Si chamber; (d) top to bottom: are SEM images of a disc shaped rotor with 85°, 160 μm deep notches and a 60° angled "bow tie" rotor.
Figure 8:
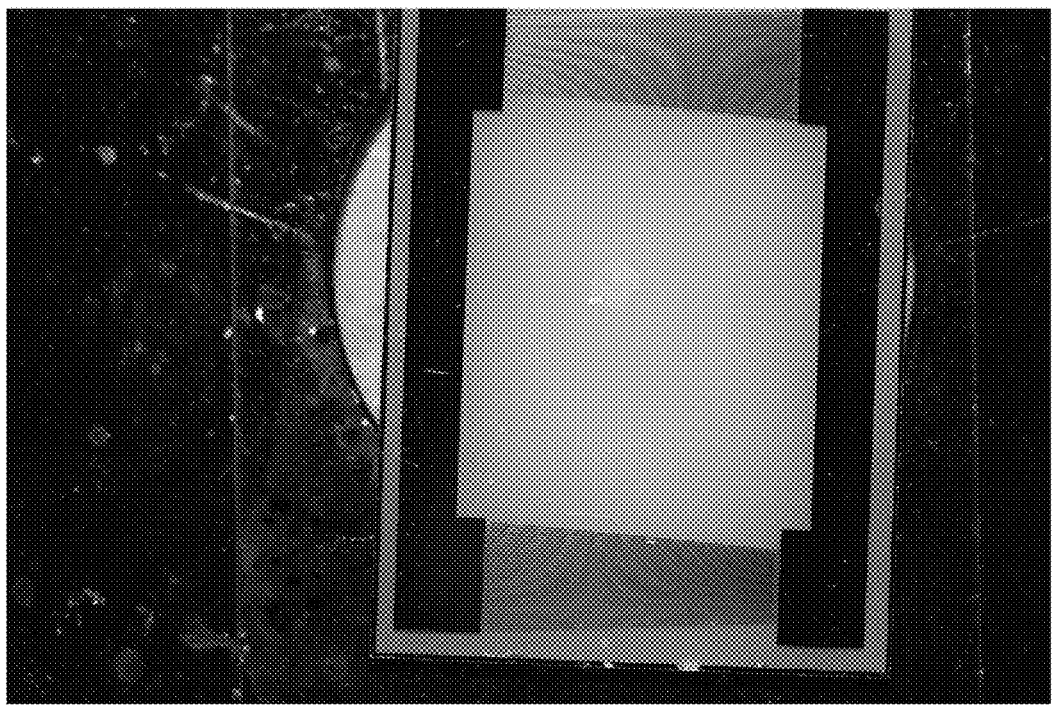
FIG. 8 shows a photograph of a substrate comprising opposing tapered interdigital transducers (T-IDTs)
Figure 9:
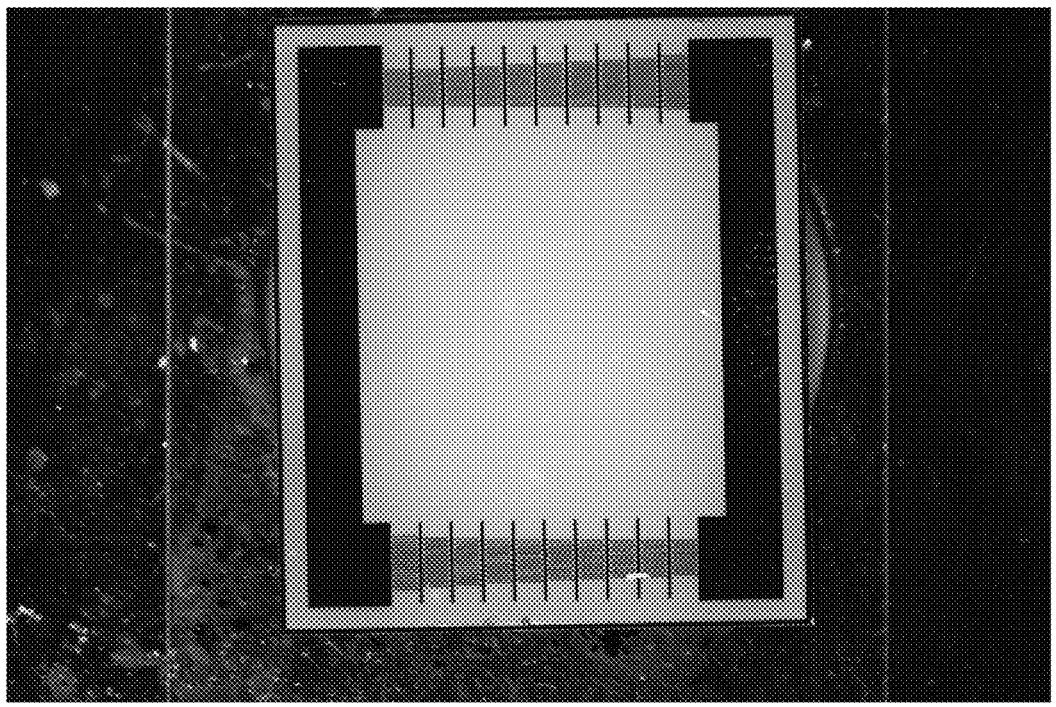
FIG. 9 shows a photograph of a substrate comprising opposing stepped interdigital transducers (S-IDTs)

Embodiments of the invention will now be further described with reference to the following examples and the figures. Examples 1 to 5 and FIGS. 1 to 6 refer to embodiments of the invention in which the rotatable platform device comprises a platform and a fluid coupling layer between the platform and the substrate, whereas Example 6 and FIG. 7 refers to embodiments of the invention in which the rotatable platform device comprises a platform in the form of a rotor that is positioned directly on the substrate.

Figure 1:
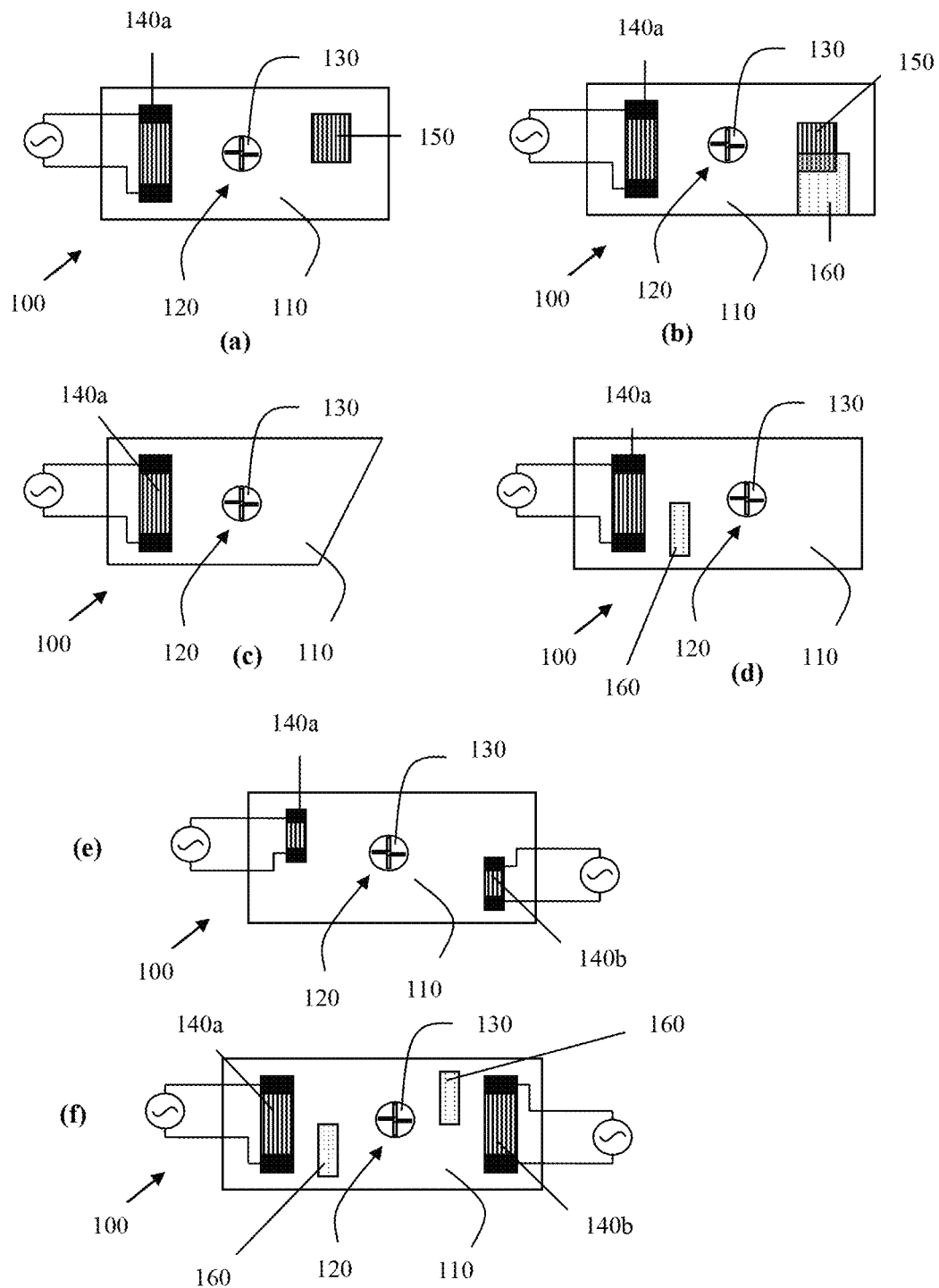
FIG. 1 (a) to (f) shows schematic diagrams of embodiments of microfluidic devices of the present invention.

Referring now generally to FIG. 1 there is shown six different configurations ((a) to (f)) of a centrifugal microfluidic device 100 of the present invention. Centrifugal microfluidic device 100 comprises a piezoelectric substrate 110 and rotatable platform device 120 on a region of the substrate 110. The rotatable platform device comprises a fluid coupling layer 125 between the substrate 110 and a rotatable platform 130. In the embodiments illustrated in FIGS. 1(a) to (d), centrifugal microfluidic device 100 includes a transducer 140a on the piezoelectric substrate 110. In the embodiments illustrated in FIGS. 1(e) and (f), centrifugal microfluidic device 100 includes a pair of opposing transducers 140a, 140b on the piezoelectric substrate 110. In each of the illustrated embodiments, there is an asymmetric distribution of surface acoustic wave radiation across the width of the fluid coupling layer 125 perpendicular to the radiation propagation direction. As a result, the surface acoustic wave contacts the fluid coupling layer 125 with a lateral distribution which causes rotation of the fluid coupling layer 125 and rotatable platform 130.

In the embodiment illustrated in FIG. 1(a) the transducer 140a is positioned substantially symmetrically with, respect to the centre of the rotatable platform device 120. A SAW reflecting device 150 is positioned on the piezoelectric substrate 110 on the other side of the rotatable platform 130 and is offset laterally with reference to the rotatable platform device 120. Surface acoustic waves generated by transducer 140a propagate on the surface of the substrate 110 and contact the fluid coupling layer 125 symmetrically. The acoustic intensity of the surface acoustic wave is lower than the threshold required to translate the fluid coupling layer 125 in the direction of the SAW and so the fluid coupling layer remains in position. Surface acoustic waves pass the fluid coupling layer 125 and part of the waves are reflected by the SAW reflecting device 150. The reflected wave then contacts the fluid coupling layer 125 and, in doing so, there is an asymmetric distribution of surface acoustic wave radiation across the width of the fluid coupling layer 125 perpendicular to the radiation propagation direction.

In the embodiment illustrated in FIG. 1(b) the transducer 140a is positioned substantially symmetrically with respect to the centre of the rotatable platform device 120. A SAW reflecting device 150 is positioned on the other side of the rotatable platform 130 and is also positioned substantially symmetrically with respect to the centre of the rotatable platform device 120. A SAW dissipating device 160 is positioned over the SAW reflecting device 150 and is offset about the centre of the rotatable platform device 120. Surface acoustic waves generated by transducer 140a propagate on the surface of the substrate 110 and contact the fluid coupling layer 125 symmetrically. Surface acoustic waves that pass the fluid coupling layer 125 are partially reflected by the SAW reflecting device 150 and the reflected wave then contacts the fluid coupling layer 125 and, in doing so, there is an asymmetric distribution of surface acoustic wave radiation across the width of the fluid coupling layer 125 perpendicular to the radiation propagation direction.

In the embodiment illustrated in FIG. 1(c) the transducer 140a is positioned substantially symmetrically with respect to the centre of the rotatable platform device 120. An end of the piezoelectric substrate 110 that is distal the end at which the transducer 140a is positioned is angled with respect to the propagation direction of the surface acoustic waves. Surface acoustic waves generated by transducer 140a propagate on the surface of the substrate 110 and contact the fluid coupling layer 125 symmetrically. Surface acoustic waves that pass the fluid coupling layer 125 are reflected at the angled end of the substrate 110 and the reflected wave then contacts the fluid coupling layer 125 and, in doing so, there is an asymmetric distribution of surface acoustic wave radiation across the width of the fluid coupling layer 125 perpendicular to the radiation propagation direction.

In the embodiment illustrated in FIG. 1(d) the transducer 140a is positioned substantially symmetrically with respect to the centre of the rotatable platform device 120. A SAW dissipating device 160 is positioned between the transducer 140a and the fluid coupling layer 125 and is offset about the centre of the rotatable platform device 120. Surface acoustic waves generated by transducer 140a propagate on the surface of the substrate 110 and are partially absorbed by the SAW dissipating device 160, resulting in an asymmetric distribution of surface acoustic wave radiation across the width of the fluid coupling layer 125 perpendicular to the radiation propagation direction.

In the embodiment illustrated in FIG. 1(e) centrifugal microfluidic device 100 includes a pair of opposing transducers 140a, 140b on the piezoelectric substrate 110 and laterally offset about the centre of the rotatable platform device 120. Surface acoustic waves generated by each of the transducers 140a, 140b propagate on the surface of the substrate 110 and contact the fluid coupling layer 125 with an asymmetric distribution of surface acoustic wave radiation across the width of the fluid coupling layer 125 perpendicular to the radiation propagation direction.

In the embodiment illustrated in FIG. 1(f) centrifugal microfluidic device 100 includes a pair of opposing transducers 140a, 140b on the piezoelectric substrate 110 and positioned on the substrate in line with the centre of the rotatable platform device 120 and a SAW dissipating device 160 is positioned between each transducer 140a, 140b and the rotatable platform device 120 such that the SAW dissipating device 160 blocks part of the surface acoustic wave that would otherwise be incident symmetrically on the fluid coupling layer 125. This results in the SAW contacting the fluid coupling layer 125 with an asymmetric distribution of surface acoustic wave radiation across the width of the fluid coupling layer 125 perpendicular to the radiation propagation direction.

Referring now more specifically to FIG. 2(a) there is shown a centrifugal microfluidic device 100 employed in the examples discussed below. Centrifugal microfluidic device 100 comprises a piezoelectric substrate 110 which in this illustrative embodiment is a Teflon®-coated lithium niobate substrate and a fluid coupling layer 125 on a region of the substrate 110 shown generally under rotatable platform 130, the rotatable platform 130 in this embodiment configured for capillary valving (see also FIG. 1(b)) and formed of thin SU-8 photoresist material with a water drop serving as the fluid coupling layer 120. Centrifugal microfluidic device 100 also includes a pair of opposing transducers 140a, 140b on the piezoelectric substrate 110 and laterally offset about the centre of the fluid coupling layer 120. In this embodiment, transducers 140a, 140b are formed as focusing transducers and in particular are configured as elliptically focusing transducers. As discussed previously, transducers 140a, 140b generate opposing surface acoustic waves that propagate on the surface of the substrate 110 and contact an edge region of the fluid coupling layer 125 to transfer energy and cause rotation of the fluid coupling layer 125 and rotatable platform 130.

Referring to FIG. 7(a) there is shown an alternative embodiment of a centrifugal microfluidic device 100 employed in the examples discussed below. The centrifugal microfluidic device 100 in this embodiment does not contain a fluid coupling layer as part of the rotatable platform device. As with the previous examples, centrifugal microfluidic device 100 comprises a piezoelectric substrate 110 which in this illustrative embodiment is a Teflon®-coated lithium niobate substrate and a rotatable platform device 120. The rotatable platform device 120 in this embodiment is configured as a rotor 130. Centrifugal microfluidic device 100 also includes a pair of opposing transducers 140a, 140b on the piezoelectric substrate 110 and laterally offset about the centre of the rotatable platform device 120. In this embodiment, transducers 140a, 140b are formed as focusing transducers and in particular are configured as elliptically focusing transducers. The rotor 130 is housed within a rotor chamber 170 which is formed on the substrate 110. The rotor 130 is journalled for rotation on a pin 180 which extends from the surface of the substrate 110. Various configuration of rotors can be used and some examples are shown in FIGS. 7(a)-(d).

Referring now generally to FIGS. 8 to 11 there is shown another alternative embodiment of a centrifugal microfluidic device 100. The centrifugal microfluidic device 100 shown in FIGS. 8, 10 and 11 comprise a pair of opposing tapered interdigital transducers 140a, 140b. The centrifugal microfluidic device 100 shown in FIG. 9 comprises a pair of opposing step interdigital transducers 140a, 140b. As with the previous examples, centrifugal microfluidic device 100 comprises a piezoelectric substrate 110 which in this illustrative embodiment is a Teflon®-coated lithium niobate substrate and a rotatable platform device 120. The pair of opposing transducers 140a, 140b on the piezoelectric substrate 110 are positioned at each end of the substrate. The finger width and or spacing of the fingers in the tapered interdigital transducers 140a and 140b tapers from adjacent one side of the substrate 110 to adjacent the opposing side of the substrate. Similarly, the finger width and or spacing of the fingers in the stepped interdigital transducers 140a, 140b step down from one side of the substrate 110 to the opposing side. The finger width and spacing of the fingers provides a specific, predetermined surface acoustic wave frequency and therefore the stepped or tapered IDTs provide a variation of frequency laterally across the device. In this way opposing edge regions of the rotatable platform device are subjected to surface acoustic waves of different frequency.

Figure 10:
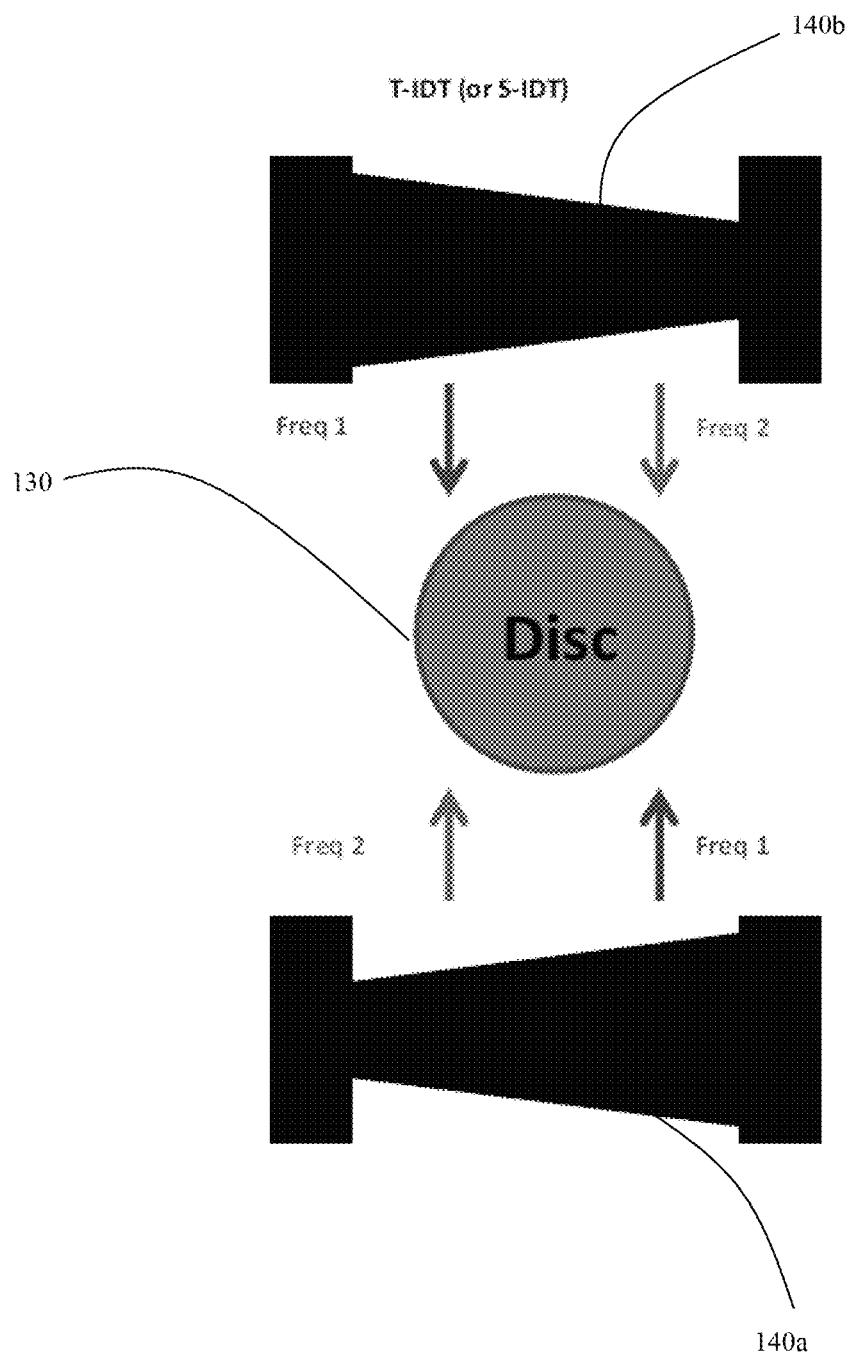
FIG. 10 shows a schematic diagram of a device having opposing tapered interdigital transducers (T-IDTs) and showing how two different frequency SAWs can be used to change the direction of rotation of the rotatable platform device.
Figure 11:
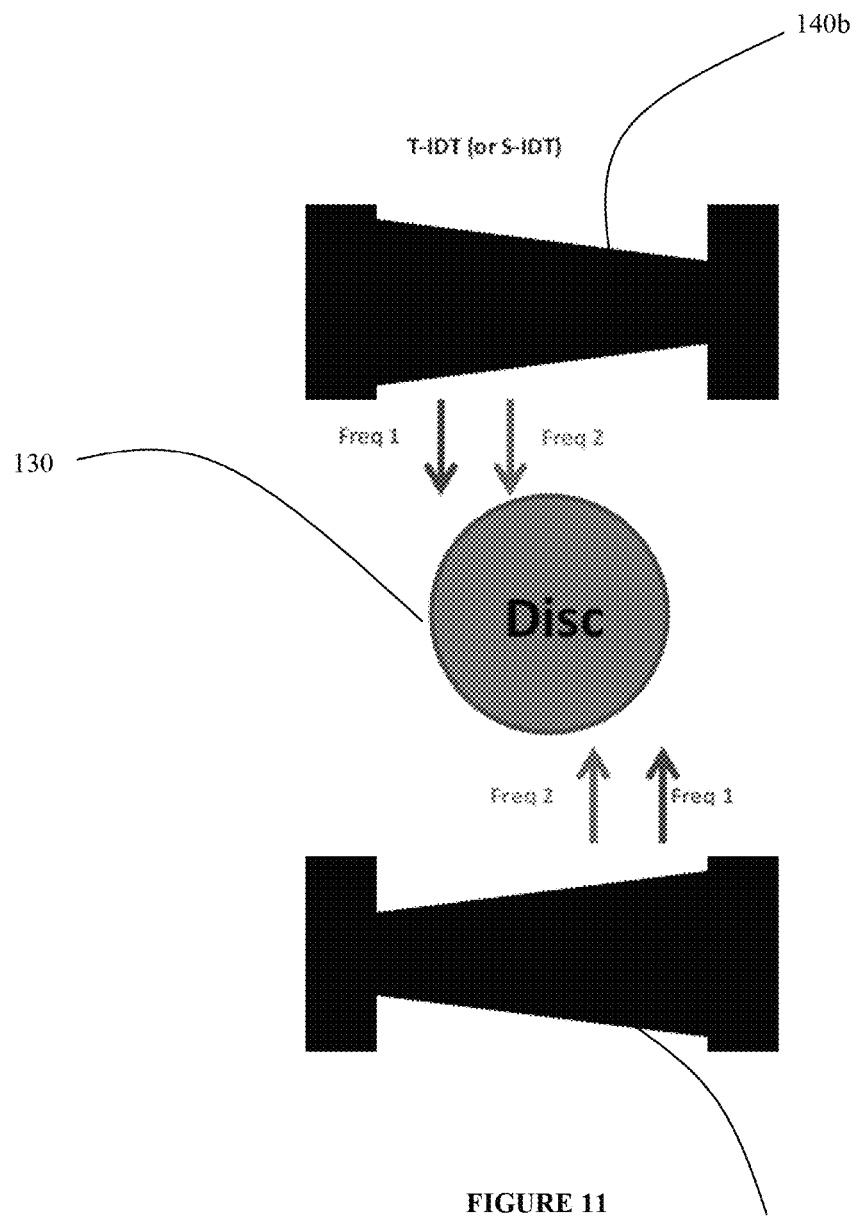
FIG. 11 shows a schematic diagram of a device having opposing tapered interdigital transducers (T-IDTs) and showing how two different frequency SAWs can be used to change the speed of rotation of the rotatable platform device.

The transducers 40a, 140b are flipped with respect to one another, meaning that the surface acoustic waves propagate in an antisymmetric fashion. These IDTs generate waves at specific positions depending on what frequency is applied to actuate the transducer. Using T-IDTs or S-IDTs in this way it is possible to change the direction of rotation of the disc by changing the frequency as depicted in FIG. 10. Furthermore, it is also possible to change the speed of rotation of the disc by changing the frequency (in addition to changing the speed of ration by changing the input voltage/power) as depicted in FIG. 11. It is also possible to focus the surface acoustic waves in the device by changing the frequency (possibly for mixing and/or particle concentration).

Materials and Methods

For the valving experiments, the rotatable platform was loaded with liquid mixtures of approximately 1:9 parts glycerol to water (glycerol was used to reduce evaporation while preparing the sample) before the rotatable platform was placed atop a small water drop pipetted onto the hydrophilic circular region of the SAW device. All other experiments employed water as the working fluid, and either mixed with food dye for the mixing tests or dispersed with fluorescent microparticles (Duke Scientific, Fremont, Calif., USA) ranging from 200 nm to 31 μm in diameter for the particle concentration studies.

To generate the SAW signal at both ends of the opposing SPUDTs, an oscillating electrical signal from a signal generator (SML-01, Rohde & Schwarz, North Ryde, NSW, Australia) was passed through an amplifier (10W1000C, Amplifier Research, Souderton, Pa., USA) and connected to each SPUDT in parallel through a pair of SMA cables and custom-made electrical contact probes. The average unloaded SAW peak amplitudes were measured with the aid of a laser Doppler vibrometer (MSA-400, Polytec GmbH, Waldbronn, Germany).

Experimental images were acquired using a variety of microscopes and cameras. High-speed rotatable platform rotation was captured by a digital camera (iSpeed, Olympus, Tokyo, Japan) attached to along working distance lens (Infinivar CFM-2/S, Infinity, Boulder, Colo., USA). The subsequent angles were then measured in ImageJ (National Institutes of Health, Bethesda, Md., USA) and the velocities calculated from this data. Images for the valve actuations were captured on a small USB camera (AM7023 Dino-Eye, AnMo Electronics Corp., Taipei, Taiwan), while mixing and particle concentration pictures were taken on a high-resolution camera (EOS 550D SLR, Canon, Tokyo, Japan). Fluorescent illumination of the particles in suspension was achieved using a simple 40 W black light (Nelson Industries, Melbourne, VIC, Australia).

Example 1—Device Fabrication

Microfluidic devices were fabricated using standard microfabrication techniques. Specifically, 127.68° Y-axis rotated, X-axis propagating lithium niobate wafers (University Wafer, South Boston, Mass., USA) were cleaned by successive sonication in acetone, isopropanol and water, followed by forced nitrogen drying. The wafers were then cleaned in a fresh piranha solution. Aluminium single-phase unidirectional transducer (SPUDT) electrodes with an elliptical focus were subsequently fabricated on the substrate using conventional photolithography and etching techniques, as shown in FIG. 1(a). The finger width and spacing of the focused SPUDTs were designed for resonance at 30 MHz, and each device on the wafer comprised an opposing SPUDT pair laterally offset by 4.5 mm to form mutually opposing acoustic radiation into the coupling layer symmetric about its centre to drive acoustic streaming and consequent azimuthal fluid motion.

The devices were then diced from the wafer using a diamond scribe (DTX, Dynatex International, Santa Rosa, Calif., USA). The pair of SPUDT electrodes and the 10 mm diameter circular region were masked with dicing tape. A Teflon® (DuPont, Wilmington, Del., USA) layer was then deposited onto the device via spin coating at 500 and 4000 rpm for 10 and 30 s, respectively, followed by the removal of the masks. The device was then baked at 80° C. for one hour, crystallising the Teflon® and forming a strongly hydrophobic surface save for the SPUDTs and the bare hydrophilic circular region where the fluid coupling drop and rotatable platform is to be placed.

Wave reflections at the edges of the device were reduced through absorption by an energy dissipating polymer (First Contact™ Polymer, Photonic Cleaning Technologies, Platteville, Wis., USA) deposited on the edges of the SAW device.

The rotatable platforms were fabricated from SU-8 photoresist (MicroChem Corp., Newton, Mass., USA) using two-step photolithography. To prevent adhesion of the SU-8 to its Si substrate and facilitate removal of the fabricated SU-8 rotatable platforms, wafers were treated with trichloro (1H,1H,2H,3H-perfluorooctyl)silane (Sigma Aldrich Pty. Ltd., Castle Hill, NSW, Australia) prior to fabrication. This was achieved through vapour deposition in a vacuum desiccator for approximately 30 min. An initial layer of SU-8 2035 was then spun onto the wafer to achieve a nominal thickness of 100 µm, followed by UV exposure to form the base of the rotatable platforms. A second layer of SU-8 2075 with an approximate thickness of 200 µm was spun and subsequently baked to form, the rotatable platform with the various microchannel patterns shown in FIGS. 1(b)-1(d) with the aid of a mask; each channel had a depth of 200 µm. Finally, the SU-8 was developed and the rotatable platforms were mechanically removed.

Example 2—Device Characterisation

Figure 2:
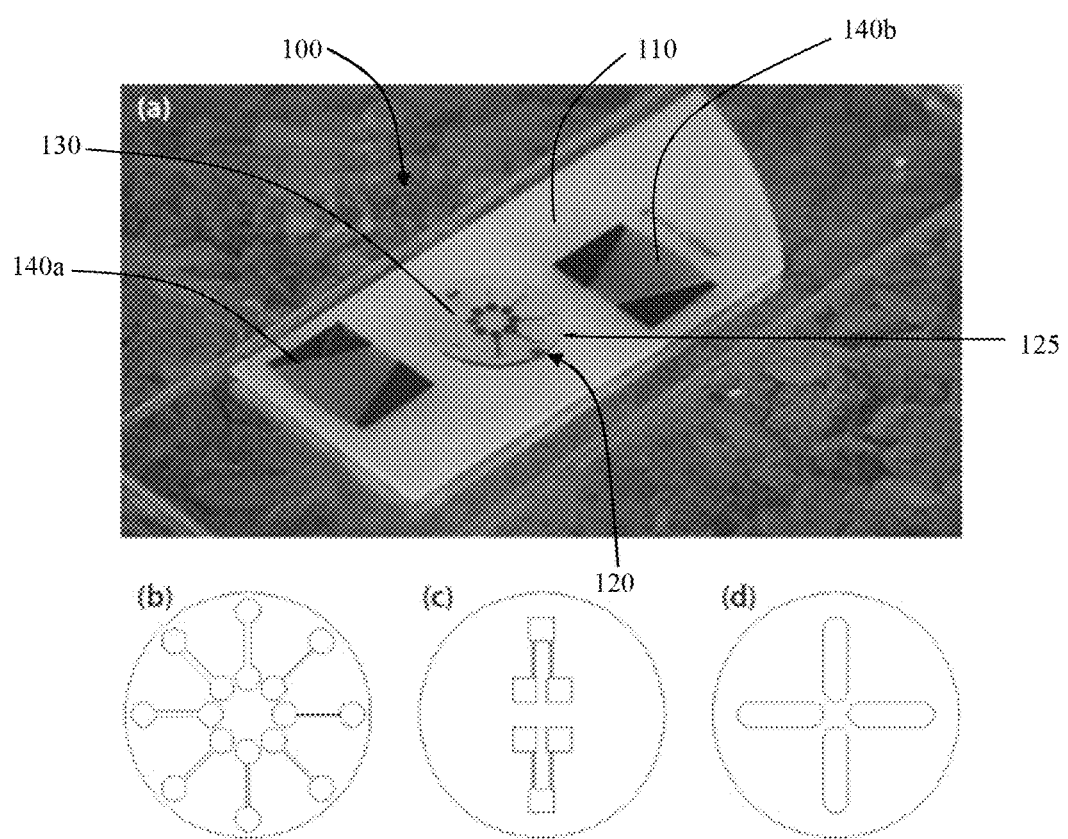
FIG. 2 (a) is a photograph of the microfluidic device comprising a pair of offset elliptically focusing transducers patterned onto a Teflon®-coated lithium niobate substrate, a water drop serving as a fluid coupling layer pipetted onto the device and confined within a masked non-hydrophobic region, and a thin SU-8 rotatable platform placed on top of the coupling layer; (b) is a schematic diagram of a microfluidic structure on the rotatable platform that is configured for capillary valving; (c) is a schematic diagram of a microfluidic structure on the rotatable platform that is configured for mixing, and (d) is a schematic diagram of a microfluidic structure on the rotatable platform that is configured for particle concentration.

Using unloaded rotatable platforms, the devices were first characterised to determine the appropriate volume of water to be used as the coupling fluid. FIG. 2 shows the rotatable platform rotation speed to be unaffected by the volume of fluid couplant used for a given input power. We observed, however, that rotatable platform precession became increasingly prevalent as the fluid volume was increased, leading to a larger variance in the data set. As such, the remainder of the experiments was carried out with a smaller fluid volume (75 µl). In addition, we also characterised the devices to determine the rotatable platform rotation speed as a function of the input power, measured through the surface displacement of the substrate as the SAW traverses. A typical response curve can be seen in FIG. 2 in which we observe the rotation speed to increase up to approximately 1400±30 rpm at a surface displacement of about 1.7 nm. Beyond this level, the precession of the rotatable platform prevented further increases in the rotatable platform rotation speed. Droplets were expelled from the meniscus of the fluid coupling layer at these large displacement amplitudes due to the large centrifugal stresses present that drove a capillary instability along the meniscus. Consequently, the experiments were conducted with surface displacements below 2 nm to ensure stability of the rotatable platform's rotation and the fluid coupling layer.

Although each of these experiments was conducted within open channels on the surface of the rotatable platforms, evaporation of the small fluid volumes in the channels and reservoirs was negligible within the short time periods that each process was performed. To further mitigate evaporative effects in the case of longer running processes, these processes could alternatively be performed in closed channels, or if necessary, carried out on heat sinks or Peltier coolers to control the device temperature.

Example 3—Capillary Valving

Figure 3:
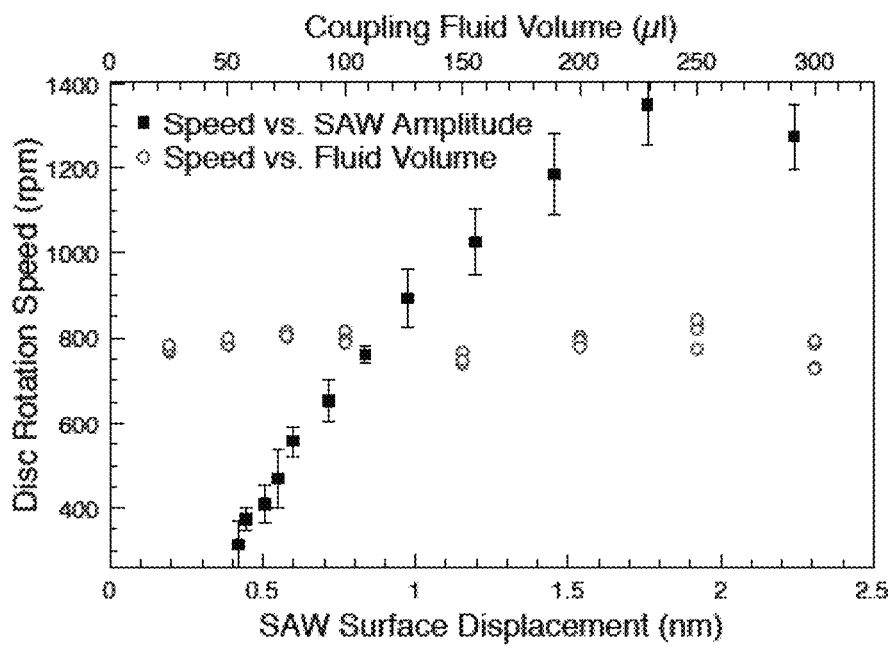
FIG. 3 is a plot showing SAW surface displacement (nm) and coupling fluid volume (μl) vs rotatable platform (disc) rotation speed (rpm). The rotatable platform rotation speed was roughly proportional to the surface displacement of the SAW substrate from about 0.5 to 1.7 nm in amplitude; beyond this value the rotation speed remained fairly constant due to rotatable platform precession and other effects. This data was taken for a fixed volume of fluid couplant (75 μl; squares). However, the rotation speed was not significantly affected by the volume of the fluid couplant used with the 10 mm rotatable platform when using a fixed surface displacement (~1 nm; circles)
Figure 4:
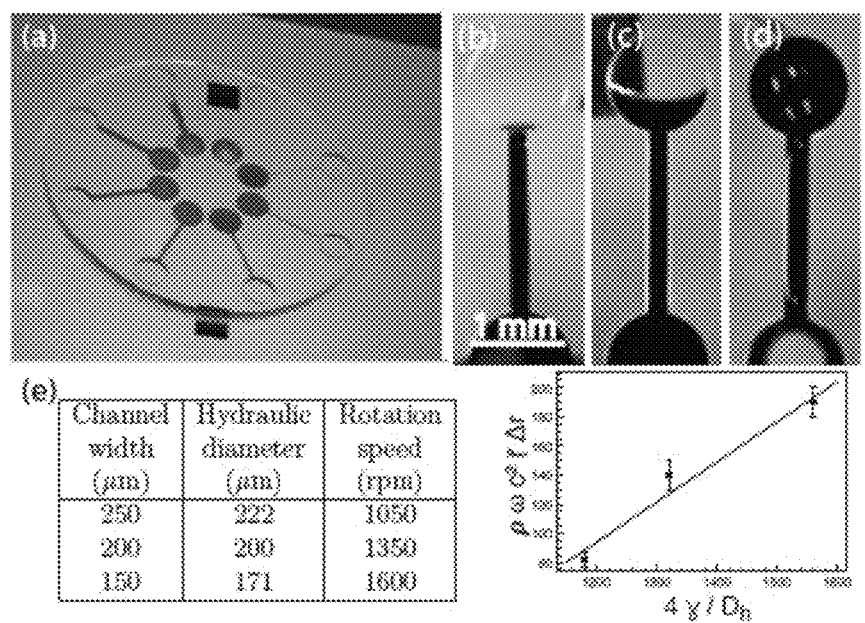
FIG. 4 (a) is a photograph showing capillary valves in the device consisting of inlet and outlet reservoirs connected by 200 mm deep channels of different widths in 'closed' position prior to rotatable platform rotation; (b), (c) and (d) are photographs showing 'opening' of a typical 200 μm wide capillary valve upon rotatable platform rotation at approximately 1350 rpm for around 20 s; the top of the images are radial locations further from the rotatable platform centre. The interval between the successive images in (b), (c) and (d) is approximately 10 s; (e) is a table and plot showing the rotation speed required to 'open' a capillary valve of a channel connected to a reservoir is inversely proportional to the width of the channel; the adjacent plot shows good agreement with the dominant force balance given by Eq. (1)
Figure 5:
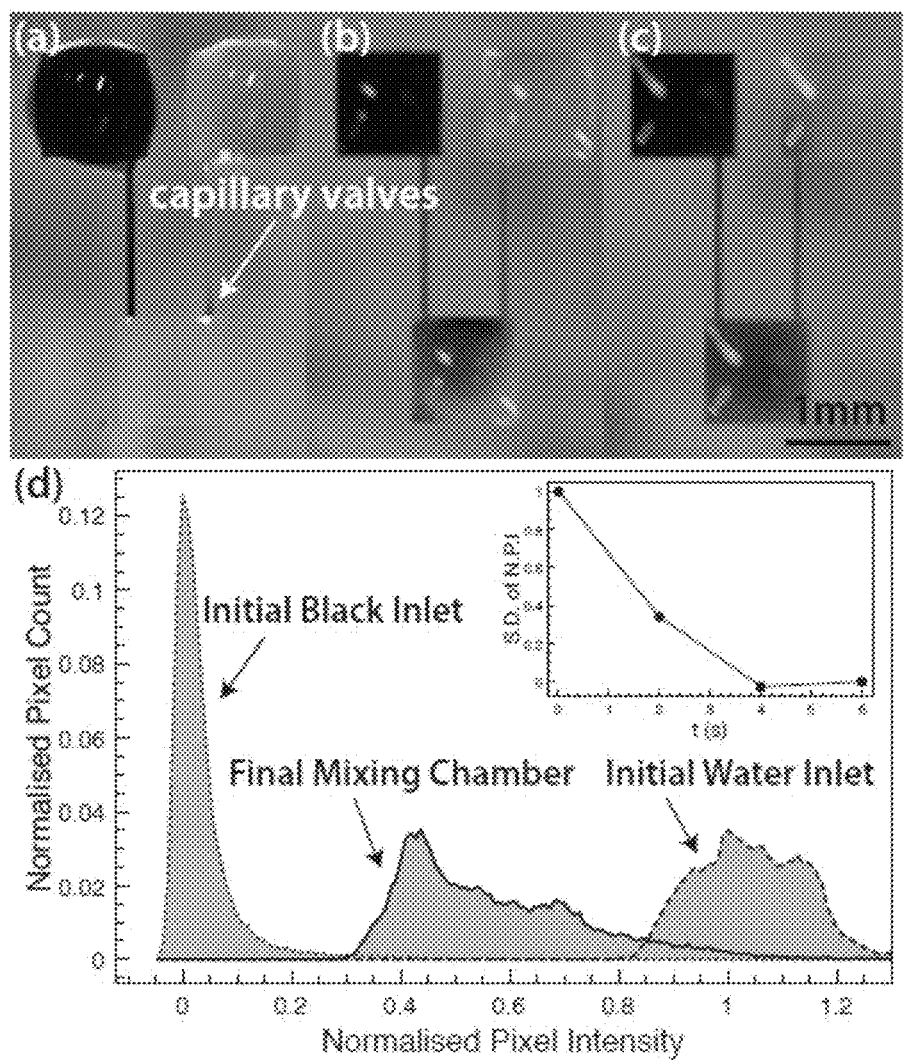
FIG. 5 (a)-(c) is a series of photographs showing mixing of two fluids using the microfluidic device. Water is placed in a pair of inlet reservoirs, one of which is also mixed with black food dye at a ratio of approximately 1:50. The inlet reservoirs are connected by channels oriented radially outwards that issue into a single outlet reservoir. (a) Upon deposition of the fluid into the inlet reservoir, the channels are observed to fill almost spontaneously. (b) During rotatable platform rotation over approximately 15 s at around 1000 rpm, the capillary valves 'open' and the outlet reservoir fills with the two fluids. (c) After further rotation, the fluids are seen to be completely mixed. For quantification, (d) a pixel intensity analysis was carried out on a 200×200 pixel region of the greyscale images, normalised against pixel intensity such that bright pixels and dark pixels had an intensity value of one and zero, respectively. The pixel count was also normalised such that the total pixel count under each distribution sums to one. The pixel intensity histograms for the inlet reservoirs containing water with and without the black dye prior to rotatable platform rotation are given by the dotted and dashed lines, respectively, whereas the corresponding histogram for the outlet reservoir is represented by the solid line and shows the emergence of an intermediate grey population between the two initial states as they mix. The inset comprises a plot of the standard deviation in the normalised pixel intensity of the outlet reservoir as a function of time, showing that the mixing completes in approximately 4 s of rotation after the reservoir was initially filled with the two fluids (when t=0 s), as ascertained when the standard deviation approaches its minimum value.
Figure 6:
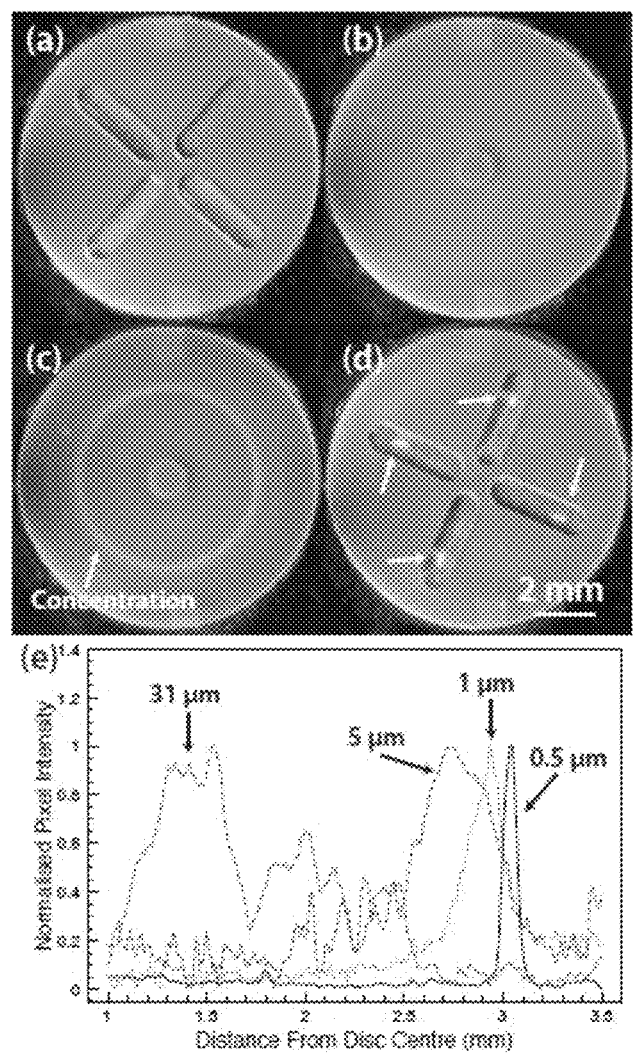
FIG. 6 (a) is a photograph showing aqueous suspensions of 5 mm fluorescent particles loaded into four separate reservoirs on the rotatable platform; (b) is a photograph showing that upon rotation of the rotatable platform at approximately 1400 rpm, we observe the particles to (c) concentrate after around 10 s, as indicated by the arrow; (d) is a photograph showing that upon relaxation of the rotatable platform rotation, we observe the 5 μm particles to remain concentrated in roughly the centre of each reservoir, as indicated by the arrows. To examine the effect of particle size on their concentration further, we placed individual suspensions of different particle sizes (200 nm, 500 nm, 1 μm, 5 μm and 31 μm) separately in each reservoir. Upon rotation of the reservoir at the same speed and over the same time interval, we observe all the particle species except the smallest 200 nm particles to collect at different locations along the centreline in each reservoir, as shown by (e) the distributions in their fluorescent intensity (as captured by the greyscale pixel intensity). The pixel intensity is normalised such that the brightest pixels due to the particle fluorescence have a value of one and the darkest pixels in the absence of particles has an intensity of zero; the data is averaged from a sequence of concentration images over four successive runs. It can therefore be seen that smaller particles concentrate more effectively (as observed by the narrower and sharper peaks in their distribution) at centreline positions further away from the centre of the rotatable platform.

Simple capillary valve operations were demonstrated on the device by designing circular inlet and outlet reservoirs connected by microfluidic channels of different widths (FIG. 1(b)). In general, fluid flows easily into the channel from the source reservoir, but not from the channel into the outer reservoir due to the restoring capillary stress imposed by the meniscus curvature at the channel aperture. The 'channel valve' therefore remains 'closed' (FIG. 3(a)) until there is sufficient radial acceleration from the rotatable platform rotation to overcome the capillary force retarding the meniscus, allowing the fluid to pass into the outer reservoir (FIG. 3(b,c,d)). A balance of the two dominant and opposing forces that govern the rotational behaviour gives $$\rho \omega_c^2 \bar{r} \Delta r = \frac{4\gamma}{D_h} a + b, \tag{1}$$

where $\rho$ is the liquid density, $\omega_c$ the critical burst frequency, i.e., the rotatable platform angular rotation speed at which the capillary valve first 'opens', $\bar{r}$ the centre of mass of the fluid in the channel, $\Delta r$ the distance from the inlet to the liquid front, $\gamma$ the surface tension of the liquid, and $D_h$ the channel hydraulic diameter, a is a non-dimensional correction factor dependent on the wetting properties and the geometry of the outlet reservoir that accounts for the non-spherical meniscus curvature and b is the pressure required to initiate the flow. The plot in FIG. 3 shows reasonable agreement of the experimental data with Eq. 1, with a=0:275 and b=−236 Pa calculated through least-squares fitting of the data to the equation. From Eq. (1), the maximum channel dimension beyond which the fluid cannot be restricted at the juncture between the channel and the output reservoir, even in the absence of rotatable platform rotation ($\omega_c$=0), is approximately 560 µm. Since the capillary stress scales inversely to the channel dimension, faster rotation is therefore required to 'open' the smaller channel valves, consistent with the results shown in FIG. 3(e).

Example 4—Mixing

By opening the capillary valves formed by two channels connecting separate inlet reservoirs into an outlet reservoir (FIG. 1(c)) upon rotation, two fluid species housed in the inlet reservoirs can be driven into the outlet reservoir and mixed. We demonstrate this concept by initially loading the reservoirs with a liquid, one containing approximately 50 ml/ml of black food dye (Queen Fine Foods, Alderley, QLD, Australia), the other simply water. In the absence of rotation, capillary filling of the channels occurred as expected, forming a blocking meniscus at the end of each channel at the entry into the outlet reservoir, as shown in FIG. 4(a). Upon rotatable platform rotation at approximately 1000 rpm, both fluids then entered the reservoir (FIG. 4(b)) and uniformly mixed into a homogenous solution upon further rotation (FIG. 4(c)).

Given that a pixel intensity analysis is a common way to show mixing efficiency between two solutions, we first converted the frames into greyscale images. A 200×200 pixel area was analysed for each of the inlet reservoirs and the single outlet reservoir. FIG. 4(d) shows the normalised pixel counts and intensities in the reservoirs prior to and after rotation (and hence mixing). The pixel intensity was normalised such that bright pixels and dark pixels had a median intensity value of one and zero, respectively. The pixel count was also normalised so that the area of each distribution is equal to unity. In addition, the inset of FIG. 4(d) shows the standard deviation of the normalised pixel intensities in the output reservoir after it filled, showing the mixing reaching completion after around 4 s of rotation at a speed of approximately 1000 rpm; the standard deviations were normalised so that the initial and final values in the inset of FIG. 4(d) were one and zero, respectively. Both FIG. 4(d) and its inset therefore clearly show that the two fluids proceeded to mix to form a solution with an intensity bracketed by the intensity values of the two inlet reservoirs. Over approximately 15 s of rotation, the outlet reservoir filled with fluid from both inlet reservoirs and a homogenous intensity roughly the average of the source fluids' intensities was generated in the outlet reservoir in just 4 s after rotatable platform rotation commenced.

Example 5—Particle Concentration

The centrifugal forces generated by platform can also be exploited to drive particle concentration and separation within reservoirs fabricated on the rotatable platform. Such operations can be useful, for example, for enhancing on-chip detection to circumvent limitations in the sensitivity that currently plague typical sensing technology. By loading the reservoirs illustrated in FIG. 1(d), each of length 3.5 mm and width 1 mm, with a dispersion of 5 μm fluorescent particles, we were able to concentrate particles at the centre of the outer region of the reservoir by spinning up the rotatable platform to approximately 1400 rpm. FIGS. 5(a) and 5(b) shows the uniform mixture of 5 μm particles in the reservoir before and at the start of rotation, respectively, whereas FIG. 5(c) shows the concentration of the particles during rotation. Upon termination of the rotatable platform rotation after 10 s, we observe the particles to remain concentrated due to van derWaals forces roughly in the centre of each reservoir.

We also examined the effect of varying the particle dimension by placing suspensions of 200 nm, 0.500 nm, 1 μm, 5 μm and 31 μm separately in each individual reservoir, followed by their collective rotation at the same speed over a similar time interval. The normalised pixel intensity plot in FIG. 5(e) quantitatively shows the location along the centreline of the reservoir where the different sized particles concentrate. We observed the four larger particle species to concentrate at different locations along the centreline of the reservoir, as observed by the peaks in their fluorescent intensity distributions shown in FIG. 5(e). Smaller particles are observed to aggregate more rapidly (not shown) at radial positions in the reservoir further from the centre of the rotatable platform. In addition, the concentration appeared to be more effective with the smaller particles, with particles more tightly aggregating into a smaller region, evident by the sharper and narrower intensity peaks in FIG. 5(e). Nevertheless, there appears to be a cut-off in the particle size with the smallest 200 nm particles failing to concentrate, and therefore remaining dispersed throughout the entire reservoir.

Example 6—Fabrication of a Device with No Fluid Coupling Layer

In this example, a rotor was housed in a chamber fabricated in Bosch deep reactive ion etched silicon (Si), bonded with UV adhesive to a double-side polished, piranha-cleaned 127.68°-Y-axis rotated, X-axis propagating lithium niobate (LN) wafer (University Wafer, South Boston, Mass., USA) on which single phase unidirectional transducers (SPUDTs) operating at 29.7 MHz were fabricated using standard UV photolithography (FIG. 1(a)). Specifically, gold (175 nm) was deposited on LN with a 5 nm chromium adhesion layer on which the SPUDTs were patterned along with alignment marks for the Si chamber. Each SPUDT had 30 finger pairs, 3 mm front end aperture and ~16Ω impedance at resonance.

The 1 mm focusing SPUDTs were positioned along the X-axis of the LN, with both facing towards the rotor chamber. To break the symmetry and hence induce rotation, each electrode was laterally offset from the centre of the rotatable platform device chamber by 0.50 mm, as shown in FIG. 1(a). The rotors were kept aligned in the chamber with a 40 μm diameter Si pin fabricated as a part of the chamber (see FIG. 1(b)). Inlet and outlet ports to the chamber were drilled with a 1 mm diameter diamond drill bit in a drill press to allow nitrogen cleaning of the chamber. The structure was closed on the top with Si; the schematic, however, shows an open structure to illustrate how the device operates.

The rotors comprised ~55 μm thick sheets of mild steel with 1 mm nominal diameter. Motors were tested with circular 'disc' shaped rotors, and with 2, 3, 4, and 5-armed impeller rotors (a selection is shown in FIGS. 1(c) and 1(d)). An initial layer of SU-8 2035 may be spun onto the rotor to achieve a nominal thickness of 100 μm, followed by UV exposure to form a base. A second layer of SU-8 2075 with an approximate thickness of 200 μm can then be spun and subsequently baked to form the rotor with suitable microchannel patterns with the aid of a mask. Finally, the SU-8 was developed and the rotatable platforms were mechanically removed.

Rotors were then placed in the Si chambers and the pieces were bonded to the LN chips with UV adhesive, with final glue thicknesses on the order of microns as measured using SEM. Owing to the opaque Si chamber housing the rotor, the device was illuminated and viewed from underneath through the transparent LN. To run the motor, an alternating current was applied at resonance to each SPUDT to generate a SAW with average surface velocities of ~1 ms$^{-1}$. The surface velocities were measured using a Laser Doppler Vibrometer across the center region where they contact the rotors (LDV, MSA (400, Polytec GmbH, Waldbronn, Germany). Rotor speeds were captured using high-speed video (Mikroton MC1310, Unterschleissheim, Germany), and rotational velocities were calculated from these videos using the software ImageJ (National Institute of Health, Bethesda, Md., USA). We note that the motor behaviour was identical in both cases of the inlet and outlet ports being open or shut: while gas pumping may have been taking place, restricting the consequent "flow" had no effect on rotor behaviour. The preload was estimated using a combination of precision scales and a vertical micropositioner by gradually releasing rotors from the substrate.

CONCLUSIONS

We have demonstrated a new class of centrifugal microfluidic lab-on-a-chip systems. The 10 mm rotatable platforms, fabricated out of SU-8 photoresist using two-step photolithography and subsequently patterned with various channel designs, are significantly smaller (by at least one order of magnitude) compared to the Lab-on-a-CD concept. In addition, all actuation components including the power supply are sufficiently small to be integrated into a solid-state, compact device that enables portable field-use. Moreover, the actuation mechanism does not involve mechanically moving parts that are commonly subject to wear and reliability issues. In place of a laboratory bench-scale motor resembling a CD player typically used in the Lab-on-a-CD platform, we drove the rotatable platform rotation by inducing azimuthal recirculation in a fluid drop on top of which the rotatable platform was placed using asymmetric surface acoustic wave radiation from a pair of transducers patterned in an offset fashion on a piezoelectric substrate. The rotatable platform rotation, at speeds up to 1400 rpm, was then used to demonstrate valving and mixing as two examples of typical microfluidic operations alongside the ability to concentrate particle suspensions to show that the Lab-on-a-CD functionality can be reproduced at these small scales for the development of truly miniaturised and portable devices for real-time field-use diagnostics and sensing.

We have also demonstrated that surface acoustic waves can be used to drive a miniaturized, 1 mm rotor at speeds exceeding 9,000 rpm and a torque of nearly 5 nN-m without a fluid coupling layer. This motor interestingly exploits adhesive stiction as an internal preload, a force usually undesirable at these scales. With additional magnetic preload, smaller rotors can be propelled to 15,000 rpm. This solid-state device has no moving parts except the rotor itself, and is sufficiently simple to allow further integration into truly miniaturized portable drive systems for potential use in microfluidic diagnostics.

It will be appreciated by persons skilled in the art that numerous variations and/or modifications may be made to the invention as shown in the specific embodiments without departing from the spirit or scope of the invention as broadly described. The present embodiments are, therefore, to be considered in all respects as illustrative and not restrictive.

Throughout this specification the word "comprise", or variations such as "comprises" or "comprising", will be understood to imply the inclusion of a stated element, integer or step, or group of elements, integers or steps, but not the exclusion of any other element, integer or step, or group of elements, integers or steps.

All publications mentioned in this specification are herein incorporated by reference. Any discussion of documents, acts, materials, devices, articles or the like which has been included in the present specification is solely for the purpose of providing a context for the present invention. It is not to be taken as an admission that any or all of these matters form part of the prior art base or were common general knowledge in the field relevant to the present invention as it existed in Australia or elsewhere before the priority date of each claim of this application.

The invention claimed is:

1. A centrifugal microfluidic device comprising:
    a piezoelectric substrate;
    a rotatable platform device on the substrate, the rotatable platform device comprising a platform and a fluid coupling layer, the fluid coupling layer positioned on a region of the substrate and between the substrate and the platform; and
    at least one transducer on the substrate, the at least one transducer being configured to generate a surface acoustic wave that propagates on a surface of the substrate and contacts the rotatable platform device asymmetrically to transfer energy thereto with a lateral distribution to cause rotation of the rotatable platform device,
    wherein the platform comprises a microfluidic structure on an upper surface thereof, the microfluidic structure comprising at least one microfluidic channel.

2. The centrifugal microfluidic device according to claim 1, wherein the at least one transducer comprises two or more transducers, each transducer being configured to generate a surface acoustic wave that propagates on the surface of the substrate and contacts an edge region of the rotatable platform device that is offset laterally with respect to a centre of the rotatable platform device.

3. The centrifugal microfluidic device according to claim 2, wherein each transducer is offset laterally with respect to a centre of the rotatable platform device and the surface acoustic wave that is generated therefrom propagates on the surface of the substrate and contacts an edge region of the rotatable platform device that is offset laterally with respect to the centre of the rotatable platform device.

4. The centrifugal microfluidic device according to claim 1, wherein the at least one transducer is offset laterally with respect to a centre of the rotatable platform device and the surface acoustic wave that is generated therefrom propagates on the surface of the substrate and contacts an edge region of the rotatable platform device that is offset laterally with respect to the centre of the rotatable platform device.

5. The centrifugal microfluidic device according to claim 1, wherein the at least one transducer is positioned on the substrate in line with a centre of the rotatable platform device and a surface acoustic wave (SAW) dissipating device is positioned between the at least one transducer and the rotatable platform device, wherein the SAW dissipating device blocks part of the surface acoustic wave that would otherwise be incident centrally on the rotatable platform device.

6. The centrifugal microfluidic device according to claim 1, wherein the piezoelectric substrate further comprises a hydrophobic surface.

7. The centrifugal microfluidic device according to claim 1, wherein the at least one transducer comprises two transducers opposing one another positioned on the piezoelectric substrate and laterally offset symmetrically about a centre of the rotatable platform device.

8. The centrifugal microfluidic device according to claim 1, wherein the at least one transducers is an interdigital transducers.

9. The centrifugal microfluidic device according to claim 1, wherein the at least one transducers is a focusing transducers.

10. The centrifugal microfluidic device according to claim 9, wherein the at least one transducers has an elliptical focus.

11. The centrifugal microfluidic device according to claim 1, wherein the at least one transducers is a tapered transducers.

12. The centrifugal microfluidic device according to claim 1, wherein the piezoelectric substrate comprises one or more lithium niobate wafers.

13. The centrifugal microfluidic device to claim 1, wherein the platform of the rotatable platform device is configured as a disc.

14. The centrifugal microfluidic device according to claim 1, wherein the microfluidic structure comprises at least one fluid reservoir in fluid communication with the at least one microfluidic channel forming a fluid flow path from the reservoir, the structure transmitting fluid from the fluid reservoir using centrifugal force due to rotation of the rotatable platform device.

15. The centrifugal microfluidic device according to claim 14, wherein the microfluidic structure further comprises a functional unit in fluid communication with the at least one microfluidic channel, the functional unit capable of receiving the fluid from the microfluidic channel and performing at least one function when in contact with the fluid.

16. A microfluidic valve comprising:
    a. piezoelectric substrate;
    a rotatable platform device on the substrate, the rotatable platform device comprising a platform and a fluid coupling layer, the fluid coupling layer positioned on a region of the substrate and between the substrate and the platform, the platform comprising a microfluidic structure comprising an inlet reservoir in fluid connection via a radially disposed microfluidic channel with an outlet reservoir, the inlet reservoir positioned radially inwardly of the outlet reservoir; and at least one transducer on the substrate, the at least one transducer being configured to generate a surface acoustic wave that propagates on a surface of the substrate and contacts the rotatable platform device asymmetrically to transfer energy thereto with a lateral distribution to cause rotation of the platform such that when the radial acceleration resulting from rotation of the platform is greater than the capillary force retarding the meniscus of a fluid in the inlet reservoir the fluid passes from the inlet reservoir to the outlet reservoir.

17. A microfluidic mixer comprising:

a piezoelectric substrate;

a rotatable platform device on the substrate, the rotatable platform device comprising a platform and a fluid coupling layer, the fluid coupling layer positioned on a region of the substrate and between the substrate and the platform, the platform comprising a microfluidic structure comprising at least two inlet reservoirs each of which is in fluid connection via a radially disposed microfluidic channel with a common outlet reservoir, the inlet reservoirs positioned radially inwardly of the outlet reservoir; and at least one transducer on the substrate, the at least one transducer being configured to generate a surface acoustic wave that propagates on a surface of the substrate and contacts the rotatable platform device asymmetrically to transfer energy thereto with a lateral distribution to, cause rotation of the platform such that when the radial acceleration resulting from rotation of the platform is, greater than the capillary force retarding the meniscus of a fluid in each of the inlet reservoirs each fluid passes from each inlet reservoir to the owlet reservoir.

* * * * *